US012343009B2

(12) United States Patent
Marecki et al.

(10) Patent No.: US 12,343,009 B2
(45) Date of Patent: Jul. 1, 2025

(54) MOTORIZED SURGICAL HANDLE ASSEMBLY

(71) Applicant: Lexington Medical, Inc., Bedford, MA (US)

(72) Inventors: Andrew Marecki, West Boylston, MA (US); Leon Amariglio, Lexington, MA (US); David Thomas Moy, Jr., Wellesley, MA (US); Richard Moyer, Allston, MA (US)

(73) Assignee: Lexington Medical, Inc., Bedford, MA (US)

( * ) Notice: Subject to any disclaimer, the term of this patent is extended or adjusted under 35 U.S.C. 154(b) by 555 days.

(21) Appl. No.: 17/833,302

(22) Filed: Jun. 6, 2022

(65) Prior Publication Data

US 2022/0387025 A1    Dec. 8, 2022

Related U.S. Application Data

(60) Provisional application No. 63/197,934, filed on Jun. 7, 2021.

(51) Int. Cl.
*A61B 17/064* (2006.01)
*A61B 17/072* (2006.01)
*A61B 17/29* (2006.01)

(52) U.S. Cl.
CPC .... *A61B 17/072* (2013.01); *A61B 2017/2926* (2013.01)

(58) Field of Classification Search
CPC .................................................. A61B 17/072
See application file for complete search history.

(56) References Cited

U.S. PATENT DOCUMENTS

| RE28,932 E | 8/1976 | Noiles et al. |
| 4,403,722 A | 9/1983 | Nikolich |

(Continued)

FOREIGN PATENT DOCUMENTS

| CN | 101507643 A | 8/2009 |
| CN | 101664331 A | 3/2010 |

(Continued)

OTHER PUBLICATIONS

International Search Report and Written Opinion received in PCT App No. PCT/US24/52666 dated Dec. 20, 2024.

(Continued)

*Primary Examiner* — Eyamindae C Jallow
(74) *Attorney, Agent, or Firm* — Perkins Coie LLP

(57) ABSTRACT

The present disclosure includes apparatuses for a motorized surgical handle assembly. An example apparatus includes a non-movable handle, a movable handle configured to be moved away from and into proximity with the non-movable handle, wherein the movable handle comprises a locking protrusion, a selector lever configured to rotate between a locked position and an unlocked position, and a selector cam coupled to the selector lever, wherein the selector cam comprises a surface with a concave locking opening, and wherein the selector cam is configured to rotate in response to the selector lever rotating, wherein, when the movable handle is in proximity with the non-movable handle and the selector lever is in the unlocked position, the surface with the concave locking opening is positioned adjacent to the locking protrusion to lock the movable handle in place.

21 Claims, 25 Drawing Sheets

(56) References Cited

U.S. PATENT DOCUMENTS

| | | |
|---|---|---|
| 4,572,419 A | 2/1986 | Klaus et al. |
| 4,725,764 A | 2/1988 | Prestel |
| 4,737,608 A | 4/1988 | Jones |
| 4,938,408 A | 7/1990 | Bedi et al. |
| 4,978,049 A | 12/1990 | Green |
| 5,300,081 A | 4/1994 | Young et al. |
| 5,326,013 A | 7/1994 | Green et al. |
| RE34,680 E | 8/1994 | Lieser |
| 5,467,911 A | 11/1995 | Tsuruta et al. |
| 5,474,223 A | 12/1995 | Viola et al. |
| 5,484,095 A | 1/1996 | Green et al. |
| 5,489,058 A | 2/1996 | Plyley et al. |
| 5,489,292 A | 2/1996 | Tovey et al. |
| 5,507,426 A | 4/1996 | Young et al. |
| 5,522,534 A | 6/1996 | Viola et al. |
| 5,535,935 A | 7/1996 | Vidal et al. |
| 5,586,711 A | 12/1996 | Plyley et al. |
| 5,588,579 A | 12/1996 | Schnut et al. |
| 5,601,224 A | 2/1997 | Bishop et al. |
| 5,736,703 A | 4/1998 | Kim |
| 5,758,814 A | 6/1998 | Gallagher et al. |
| 5,762,256 A | 6/1998 | Mastri et al. |
| 5,799,857 A | 9/1998 | Robertson et al. |
| 5,823,066 A | 10/1998 | Huitema et al. |
| 5,836,503 A | 11/1998 | Ehrenfels et al. |
| 5,865,361 A | 2/1999 | Milliman et al. |
| 5,901,895 A | 5/1999 | Heaton et al. |
| 6,109,500 A | 8/2000 | Alli et al. |
| 6,281,453 B1 | 8/2001 | Uleski |
| 6,302,798 B1 | 10/2001 | Nakaguro et al. |
| 6,905,057 B2 | 6/2005 | Swayze et al. |
| 6,945,444 B2 | 9/2005 | Gresham et al. |
| 6,957,758 B2 | 10/2005 | Aranyi |
| 7,044,352 B2 | 5/2006 | Shelton et al. |
| 7,044,353 B2 | 5/2006 | Mastri et al. |
| 7,083,075 B2 | 8/2006 | Swayze et al. |
| 7,097,089 B2 | 8/2006 | Marczyk |
| 7,128,254 B2 | 10/2006 | Shelton et al. |
| 7,143,923 B2 | 12/2006 | Shelton et al. |
| 7,143,924 B2 | 12/2006 | Scirica et al. |
| 7,168,604 B2 | 1/2007 | Milliman et al. |
| 7,225,963 B2 | 6/2007 | Scirica |
| 7,225,964 B2 | 6/2007 | Mastri et al. |
| 7,234,624 B2 | 6/2007 | Gresham et al. |
| 7,246,734 B2 | 7/2007 | Shelton |
| 7,303,106 B2 | 12/2007 | Milliman et al. |
| 7,325,713 B2 | 2/2008 | Aranyi |
| 7,364,060 B2 | 4/2008 | Milliman |
| 7,380,695 B2 | 6/2008 | Doll et al. |
| 7,380,696 B2 | 6/2008 | Shelton et al. |
| 7,398,907 B2 | 7/2008 | Racenet et al. |
| 7,404,508 B2 | 7/2008 | Smith et al. |
| 7,416,101 B2 | 8/2008 | Shelton et al. |
| RE40,514 E | 9/2008 | Mastri et al. |
| 7,422,136 B1 | 9/2008 | Marczyk |
| 7,455,208 B2 | 11/2008 | Wales et al. |
| 7,490,749 B2 | 2/2009 | Schall et al. |
| 7,494,038 B2 | 2/2009 | Milliman |
| 7,516,877 B2 | 4/2009 | Aranyi |
| 7,546,940 B2 | 6/2009 | Milliman et al. |
| 7,611,038 B2 | 11/2009 | Racenet et al. |
| 7,624,902 B2 | 12/2009 | Marczyk et al. |
| 7,658,311 B2 | 2/2010 | Boudreaux |
| 7,694,865 B2 | 4/2010 | Scirica |
| 7,753,245 B2 | 7/2010 | Boudreaux et al. |
| 7,780,055 B2 | 8/2010 | Scirica et al. |
| 7,784,663 B2 | 8/2010 | Shelton |
| 7,794,475 B2 | 9/2010 | Hess et al. |
| 7,802,712 B2 | 9/2010 | Milliman et al. |
| 7,819,296 B2 | 10/2010 | Hueil et al. |
| 7,824,426 B2 | 11/2010 | Racenet et al. |
| 7,832,408 B2 | 11/2010 | Shelton et al. |
| 7,837,079 B2 | 11/2010 | Holsten et al. |
| 7,845,535 B2 | 12/2010 | Scircia |
| 7,857,187 B2 | 12/2010 | Milliman |
| 7,922,063 B2 | 4/2011 | Zemlok et al. |
| 7,926,692 B2 | 4/2011 | Racenet et al. |
| 7,963,431 B2 | 6/2011 | Scirica |
| 7,967,178 B2 | 6/2011 | Scirica et al. |
| 7,967,180 B2 | 6/2011 | Scirica |
| 8,020,743 B2 | 9/2011 | Shelton |
| 8,056,789 B1 | 11/2011 | White et al. |
| 8,061,576 B2 | 11/2011 | Cappola |
| 8,070,036 B1 | 12/2011 | Knodel |
| 8,070,836 B2 | 12/2011 | Ng et al. |
| 8,123,101 B2 | 2/2012 | Racenet et al. |
| 8,136,712 B2 | 3/2012 | Zingman |
| 8,141,763 B2 | 3/2012 | Milliman |
| 8,157,148 B2 | 4/2012 | Scirica |
| 8,186,555 B2 | 5/2012 | Shelton et al. |
| 8,210,411 B2 | 7/2012 | Yates et al. |
| 8,235,274 B2 | 8/2012 | Cappola |
| 8,292,157 B2 | 10/2012 | Smith et al. |
| 8,308,040 B2 | 11/2012 | Huang et al. |
| 8,328,822 B2 | 12/2012 | Huitema et al. |
| 8,336,751 B2 | 12/2012 | Scirica |
| 8,336,754 B2 | 12/2012 | Cappola et al. |
| 8,342,378 B2 | 1/2013 | Marczyk et al. |
| 8,360,296 B2 | 1/2013 | Zingman |
| 8,413,868 B2 | 4/2013 | Pigorini |
| 8,413,868 B2 | 4/2013 | Cappola |
| 8,414,577 B2 | 4/2013 | Boudreaux et al. |
| 8,424,736 B2 | 4/2013 | Scirica et al. |
| 8,499,992 B2 | 8/2013 | Whitman et al. |
| 8,506,557 B2 | 8/2013 | Zemlok et al. |
| 8,517,241 B2 | 8/2013 | Nicholas et al. |
| 8,573,460 B2 | 11/2013 | Cappola |
| 8,573,463 B2 | 11/2013 | Scirica et al. |
| 8,574,463 B2 | 11/2013 | Tani et al. |
| 8,584,919 B2 | 11/2013 | Hueil et al. |
| 8,608,043 B2 | 12/2013 | Scirica |
| 8,608,045 B2 | 12/2013 | Smith et al. |
| 8,622,894 B2 | 1/2014 | Banik et al. |
| 8,672,205 B2 | 3/2014 | Leitner |
| 8,684,247 B2 | 4/2014 | Scirica et al. |
| 8,684,249 B2 | 4/2014 | Racenet et al. |
| 8,685,004 B2 | 4/2014 | Zemlock et al. |
| 8,695,865 B2 | 4/2014 | Smith et al. |
| 8,708,211 B2 | 4/2014 | Zemlock et al. |
| 8,708,213 B2 | 4/2014 | Shelton et al. |
| 8,806,973 B2 | 8/2014 | Ross et al. |
| 8,820,607 B2 | 9/2014 | Marczyk |
| 8,888,762 B2 | 11/2014 | Whitman |
| 8,888,814 B2 | 11/2014 | Cappola |
| 8,894,647 B2 | 11/2014 | Beardsley et al. |
| 8,910,847 B2 | 12/2014 | Nalagatla et al. |
| 8,925,783 B2 | 1/2015 | Zemlok et al. |
| 9,113,876 B2 | 8/2015 | Zemlok et al. |
| 9,155,529 B2 | 10/2015 | Beardsley et al. |
| 9,204,876 B2 | 12/2015 | Cappola et al. |
| 9,232,944 B2 | 1/2016 | Cappola et al. |
| 9,265,585 B2 | 2/2016 | Wingardner et al. |
| 9,320,519 B1 | 4/2016 | Knodel |
| 9,364,218 B2 | 6/2016 | Scirica |
| 9,364,226 B2 | 6/2016 | Zemlok et al. |
| 9,393,016 B2 | 7/2016 | Scirica et al. |
| 9,445,810 B2 | 9/2016 | Cappola |
| 9,465,873 B1 | 10/2016 | Franke et al. |
| 9,474,528 B2 | 10/2016 | Marczyk |
| 9,498,216 B2 | 11/2016 | Williams |
| 9,522,029 B2 | 12/2016 | Yates et al. |
| 9,539,006 B2 | 1/2017 | Collings et al. |
| 9,554,803 B2 | 1/2017 | Smith et al. |
| 9,629,623 B2 | 4/2017 | Lytle et al. |
| 9,636,091 B2 | 5/2017 | Beardsley et al. |
| 9,655,617 B2 | 5/2017 | Cappola |
| 9,668,731 B2 | 6/2017 | Zemlok et al. |
| 9,668,735 B2 | 6/2017 | Beetel |
| 9,820,738 B2 | 11/2017 | Lytle et al. |
| 9,839,425 B2 | 12/2017 | Zergiebel et al. |
| 9,861,358 B2 | 1/2018 | Marczyk et al. |
| 9,867,675 B2 | 1/2018 | Beardsley et al. |
| 9,872,673 B2 | 1/2018 | Beardsley et al. |
| 9,918,713 B2 | 3/2018 | Zergiebel et al. |

(56) References Cited

U.S. PATENT DOCUMENTS

| | | | |
|---|---|---|---|
| 9,931,739 B2 | 4/2018 | Nelson et al. | |
| 9,968,276 B2 | 5/2018 | Koktzoglou | |
| 9,987,029 B2 | 6/2018 | Beardsley et al. | |
| 9,993,258 B2 | 6/2018 | Shelton et al. | |
| 10,004,504 B2 | 6/2018 | Bryant | |
| 10,098,637 B2 | 10/2018 | Zergiebel et al. | |
| 10,105,139 B2 | 10/2018 | Yates et al. | |
| 10,383,634 B2 | 8/2019 | Shelton et al. | |
| 10,433,842 B2 | 10/2019 | Amariglio et al. | |
| 10,856,871 B2 | 12/2020 | Somekh et al. | |
| 11,103,247 B2 | 8/2021 | Amariglio et al. | |
| 11,166,723 B2 | 11/2021 | Somekh et al. | |
| 11,617,583 B2 | 4/2023 | Somekh et al. | |
| 11,622,764 B2 | 4/2023 | Marecki et al. | |
| 12,089,846 B2 | 9/2024 | Marecki et al. | |
| 2001/0030219 A1 | 10/2001 | Green et al. | |
| 2004/0232199 A1 | 11/2004 | Shelton et al. | |
| 2005/0006429 A1 | 1/2005 | Wales et al. | |
| 2005/0116009 A1 | 6/2005 | Milliman | |
| 2006/0079912 A1 | 4/2006 | Whitfield et al. | |
| 2006/0111210 A1 | 5/2006 | Hinman | |
| 2007/0125826 A1 | 6/2007 | Shelton | |
| 2007/0257080 A1 | 11/2007 | Kamins et al. | |
| 2007/0262116 A1 | 11/2007 | Hueil et al. | |
| 2008/0017693 A1 | 1/2008 | Mastri et al. | |
| 2008/0083810 A1 | 4/2008 | Marczyk | |
| 2008/0179374 A1 | 7/2008 | Beardsley et al. | |
| 2008/0296346 A1 | 12/2008 | Shelton et al. | |
| 2008/0314958 A1 | 12/2008 | Scirica | |
| 2009/0062614 A1 | 3/2009 | Adzich et al. | |
| 2009/0145947 A1 | 6/2009 | Scirica et al. | |
| 2009/0272614 A1 | 11/2009 | Watarai | |
| 2010/0001036 A1 | 1/2010 | Marczyk et al. | |
| 2010/0012700 A1 | 1/2010 | Perron et al. | |
| 2010/0264193 A1 | 10/2010 | Huang et al. | |
| 2011/0009850 A1 | 1/2011 | Main et al. | |
| 2011/0062211 A1 | 3/2011 | Ross et al. | |
| 2011/0166585 A1 | 7/2011 | Roth et al. | |
| 2011/0253765 A1 | 10/2011 | Nicholas et al. | |
| 2011/0290854 A1 | 12/2011 | Timm et al. | |
| 2011/0295313 A1 | 12/2011 | Kerr | |
| 2012/0074194 A1 | 3/2012 | Miller et al. | |
| 2012/0080477 A1 | 4/2012 | Leimbach et al. | |
| 2012/0116391 A1 | 5/2012 | Houser et al. | |
| 2012/0286019 A1 | 11/2012 | Hueil et al. | |
| 2012/0286020 A1 | 11/2012 | Smith et al. | |
| 2012/0293103 A1 | 11/2012 | Forster et al. | |
| 2013/0030428 A1* | 1/2013 | Worrell | A61B 5/0205 |
| | | | 606/208 |
| 2013/0053831 A1 | 2/2013 | Johnson et al. | |
| 2013/0092719 A1 | 4/2013 | Kostrzewski | |
| 2013/0098966 A1 | 4/2013 | Kostrzewski et al. | |
| 2013/0168435 A1 | 7/2013 | Huang et al. | |
| 2013/0199327 A1 | 8/2013 | Park et al. | |
| 2013/0245676 A1 | 9/2013 | Cappola | |
| 2013/0304115 A1 | 11/2013 | Miyamoto | |
| 2014/0001231 A1 | 1/2014 | Shelton et al. | |
| 2014/0148803 A1 | 5/2014 | Taylor | |
| 2014/0224856 A1 | 8/2014 | Smith et al. | |
| 2014/0263543 A1* | 9/2014 | Leimbach | A61B 34/30 |
| | | | 227/175.2 |
| 2014/0276949 A1 | 9/2014 | Staunton et al. | |
| 2014/0305988 A1 | 10/2014 | Boudreaux et al. | |
| 2014/0305994 A1 | 10/2014 | Parihar et al. | |
| 2015/0053749 A1 | 2/2015 | Shelton et al. | |
| 2015/0196966 A1 | 7/2015 | Tsai | |
| 2015/0196996 A1 | 7/2015 | Nelson et al. | |
| 2015/0209059 A1 | 7/2015 | Trees et al. | |
| 2015/0297216 A1 | 10/2015 | Williams | |
| 2015/0342605 A1 | 12/2015 | Abbott et al. | |
| 2015/0374396 A1 | 12/2015 | Strobl et al. | |
| 2016/0058441 A1 | 3/2016 | Morgan et al. | |
| 2016/0074106 A1 | 3/2016 | Garrison | |
| 2016/0089175 A1 | 3/2016 | Hibner et al. | |
| 2016/0166250 A1 | 6/2016 | Marczyk | |
| 2016/0249945 A1 | 9/2016 | Shelton et al. | |
| 2016/0270786 A1 | 9/2016 | Scirica | |
| 2017/0000485 A1 | 1/2017 | Shelton et al. | |
| 2017/0172577 A1 | 6/2017 | Wenchell et al. | |
| 2017/0224334 A1* | 8/2017 | Worthington | A61B 17/32 |
| 2017/0224343 A1* | 8/2017 | Baxter, III | A61B 17/072 |
| 2017/0252096 A1 | 9/2017 | Felder et al. | |
| 2017/0281177 A1 | 10/2017 | Harris et al. | |
| 2017/0281184 A1 | 10/2017 | Shelton et al. | |
| 2017/0281220 A1 | 10/2017 | Hibner et al. | |
| 2018/0021041 A1 | 1/2018 | Zhang et al. | |
| 2018/0021082 A1 | 1/2018 | Trees et al. | |
| 2018/0042637 A1 | 2/2018 | Craig et al. | |
| 2018/0078354 A1 | 3/2018 | Cardinale et al. | |
| 2018/0091145 A1 | 3/2018 | Dey et al. | |
| 2018/0168599 A1 | 6/2018 | Bakos et al. | |
| 2018/0289370 A1 | 10/2018 | Amariglio et al. | |
| 2018/0310935 A1 | 11/2018 | Wixey | |
| 2018/0317915 A1 | 11/2018 | Mcdonald | |
| 2018/0368832 A1 | 12/2018 | Marecki et al. | |
| 2019/0183491 A1 | 6/2019 | Shelton et al. | |
| 2019/0261984 A1 | 8/2019 | Nelson et al. | |
| 2019/0290265 A1 | 9/2019 | Shelton et al. | |
| 2020/0008801 A1 | 1/2020 | Somekh et al. | |
| 2020/0015818 A1 | 1/2020 | Amariglio et al. | |
| 2020/0046362 A1 | 2/2020 | Baril et al. | |
| 2020/0093486 A1 | 3/2020 | Somekh et al. | |
| 2020/0222046 A1 | 7/2020 | Somekh et al. | |
| 2020/0405293 A1 | 12/2020 | Shelton et al. | |
| 2021/0007740 A1 | 1/2021 | Marecki et al. | |
| 2021/0085323 A1 | 3/2021 | Somekh et al. | |
| 2021/0346021 A1 | 11/2021 | Amariglio et al. | |
| 2022/0133318 A1 | 5/2022 | Hudson et al. | |
| 2022/0183688 A1 | 6/2022 | Moy et al. | |
| 2022/0218335 A1 | 7/2022 | Baxter et al. | |
| 2022/0338874 A1 | 10/2022 | Marecki et al. | |
| 2022/0387025 A1* | 12/2022 | Marecki | A61B 17/072 |
| 2023/0092719 A1 | 3/2023 | Marbach et al. | |
| 2023/0165584 A1 | 6/2023 | Leimbach et al. | |
| 2023/0233207 A1 | 7/2023 | Somekh et al. | |
| 2023/0233208 A1 | 7/2023 | Marecki et al. | |
| 2023/0371954 A1 | 11/2023 | Bear et al. | |
| 2024/0050093 A1 | 2/2024 | Marecki et al. | |
| 2025/0009352 A1 | 1/2025 | Marecki et al. | |

FOREIGN PATENT DOCUMENTS

| | | |
|---|---|---|
| CN | 1985768 B | 9/2011 |
| CN | 101194853 B | 7/2012 |
| CN | 101965156 B | 12/2012 |
| CN | 108542464 A | 9/2018 |
| DE | 112019002420 T5 | 3/2021 |
| EP | 1563791 A1 | 8/2005 |
| EP | 1563792 A1 | 8/2005 |
| EP | 1563794 A1 | 8/2005 |
| EP | 1709911 A1 | 10/2006 |
| EP | 1021130 B1 | 11/2006 |
| EP | 1908410 A1 | 4/2008 |
| EP | 2253277 A1 | 11/2010 |
| EP | 2253278 A1 | 11/2010 |
| EP | 2586382 A3 | 9/2013 |
| EP | 2777530 A1 | 9/2014 |
| EP | 2839786 A1 | 2/2015 |
| EP | 2886020 A1 | 6/2015 |
| EP | 2886071 A1 | 6/2015 |
| EP | 2484290 B1 | 7/2015 |
| EP | 2942022 A1 | 11/2015 |
| EP | 2311385 B1 | 5/2017 |
| WO | 2004075728 A2 | 9/2004 |
| WO | 2016107586 A1 | 7/2016 |
| WO | 2018035796 A1 | 3/2018 |

OTHER PUBLICATIONS

Final Office Action received in U.S. Appl. No. 15/481,949 dated May 29, 2019, 15 pages.

International Search Report and Written Opinion dated Apr. 7, 2020

(56) References Cited

OTHER PUBLICATIONS for PCT Application No. PCT/US2020/013694 filed Jan. 15, 2020, 8 pages.
International Search Report and Written Opinion dated Jun. 18, 2018 for PCT Application No. PCT/US2018/025988 filed Apr. 4, 2018, 8 pages.
International Search Report and Written Opinion dated May 25, 2023 for PCT Application No. PCT/US2023/014366 Filed Mar. 2, 2013, 8 pages.
International Search Report and Written Opinion dated Oct. 22, 2018 for PCT Application No. PCT/US2018/038909 filed Jun. 22, 2018, 10 pages.
International Search Report and Written Opinion dated Oct. 4, 2019 for PCT Application No. PCT/US2019/040315 filed Jul. 2, 2018, 9 pages.
International Search Report and Written Opinion received in PCT/US2022/032434 dated Oct. 19, 2022, 11 pages.
Non Final Office Action received in U.S. Appl. No. 15/481,949 dated Mar. 18, 2019, 22 pages.
Non Final Office Action received in U.S. Appl. No. 16/249,520 dated Jul. 27, 2020, 10 pages.
Non Final Office Action received in U.S. Appl. No. 17/113,865 dated Sep. 19, 2022, 13 pages.
Non Final Office Action received in U.S. Appl. No. 17/241,538 dated Aug. 16, 2022, 10 pages.
Non Final Office Action received in U.S. Appl. No. 17/382,705 dated Sep. 24, 2024, 10 pages.
Non Final Office Action received in U.S. Appl. No. 17/686,730 dated Jan. 8, 2024, 10 pages.
Non Final Office Action received in U.S. Appl. No. 18/129,317 dated Dec. 8, 2023, 8 pages.
Non Final Office Action received in U.S. Appl. No. 18/129,324 dated Jan. 19, 2024, 9 pages.
Notice of Allowance received in U.S. Appl. No. 16/249,520 dated Nov. 3, 2020, 8 pages.
Notice of Allowance received in U.S. Appl. No. 16/577,097 dated Sep. 13, 2021, 8 pages.
Notice of Allowance received in U.S. Appl. No. 16/582,829 dated May 14, 2021, 7 pages.
Notice of Allowance received in U.S. Appl. No. 17/133,865 dated Dec. 7, 2022; 9 pages.
Notice of Allowance received in U.S. Appl. No. 17/241,538 dated Jan. 11, 2023, 9 pages.
Notice of Allowance received in U.S. Appl. No. 17/686,730 dated Apr. 16, 2024, 7 pages.
Notice of Allowance received in U.S. Appl. No. 17/686,730 dated Aug. 5, 2024, 8 pages.
Notice of Allowance received in U.S. Appl. No. 18/125,314 dated Nov. 8, 2024, 19 pages.
Notice of Allowance received in U.S. Appl. No. 18/129,317 dated Jul. 17, 2024, 7 pages.
Notice of Allowance received in U.S. Appl. No. 18/129,317 dated Mar. 21, 2024, 7 pages.
Notice of Allowance received in U.S. Appl. No. 18/129,324 dated May 15, 2024, 7 pages.
Notice of Allowance received in U.S. Appl. No. 15/481,949 dated Aug. 14, 2019, 10 pages.
Restriction Requirement received in U.S. Appl. No. 17/382,705 dated May 8, 2024, 6 pages.
Restriction Requirement received in U.S. Appl. No. 18/496,107 dated Sep. 24, 2024, 14 pages.
Non-Final Office Action received in U.S. Appl. No. 18/496,107 dated Dec. 12, 2024, 55 pages.
Notice of Allowance received in U.S. Appl. No. 17/382,705 dated Mar. 5, 2025, 37 pages.
Notice of Allowance received in U.S. Appl. No. 18/129,317 dated Feb. 18, 2025, 13 pages.
Final Office Action received in U.S. Appl. No. 18/496,107 dated Apr. 7, 2025, 35 pages.

\* cited by examiner

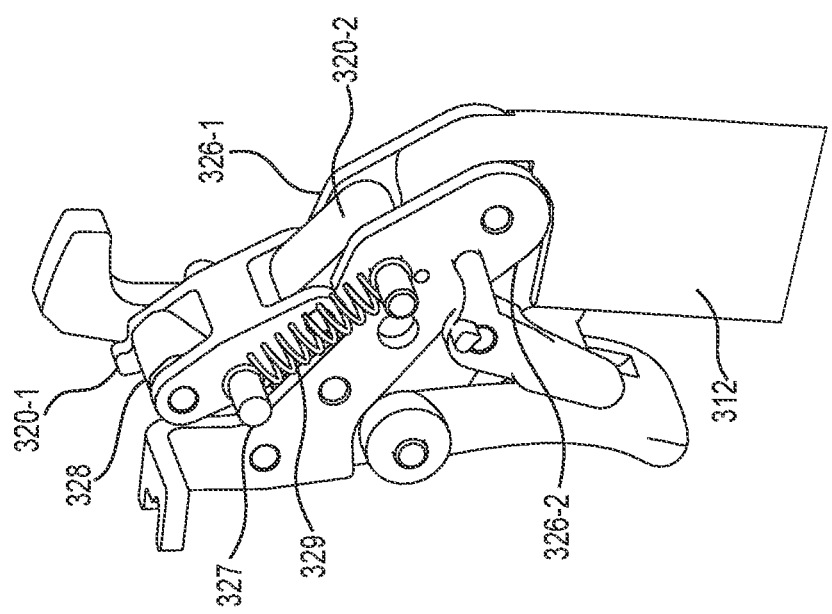

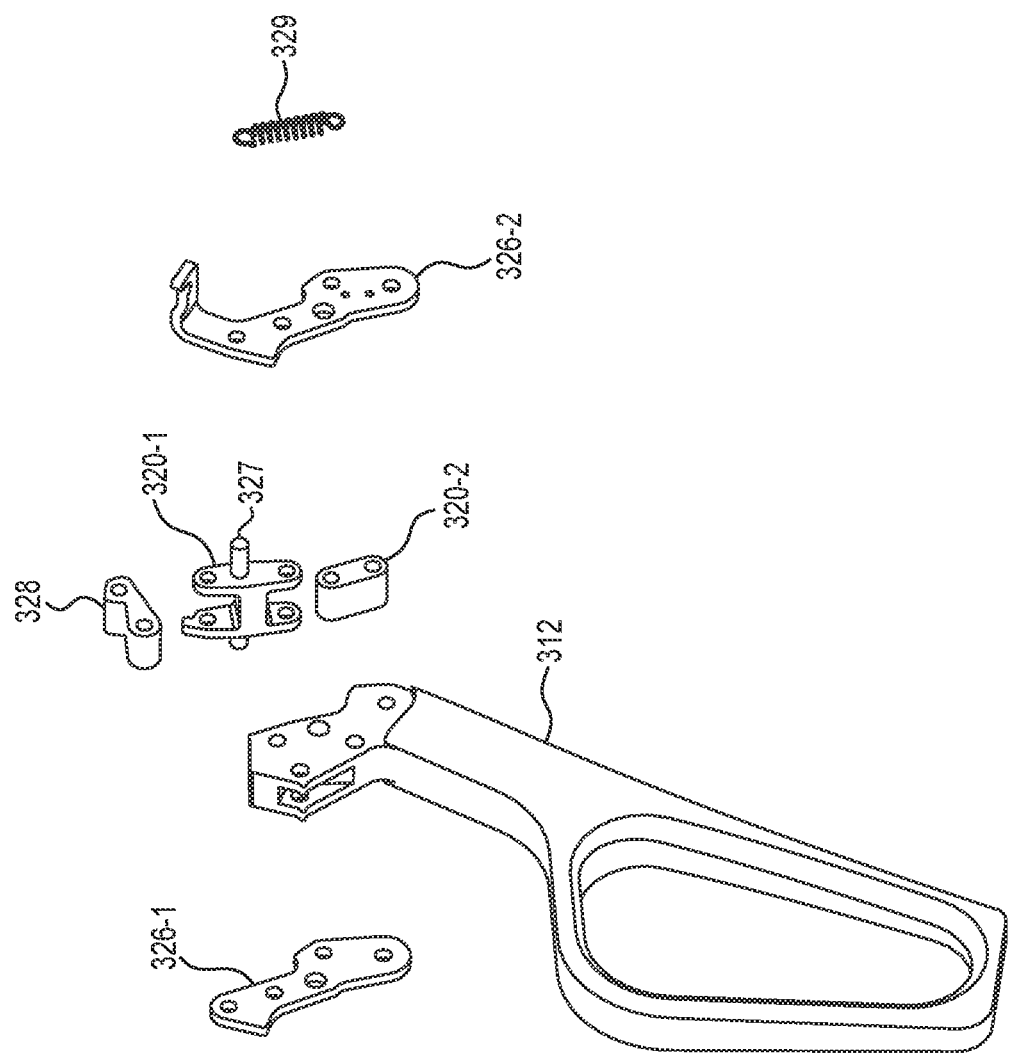

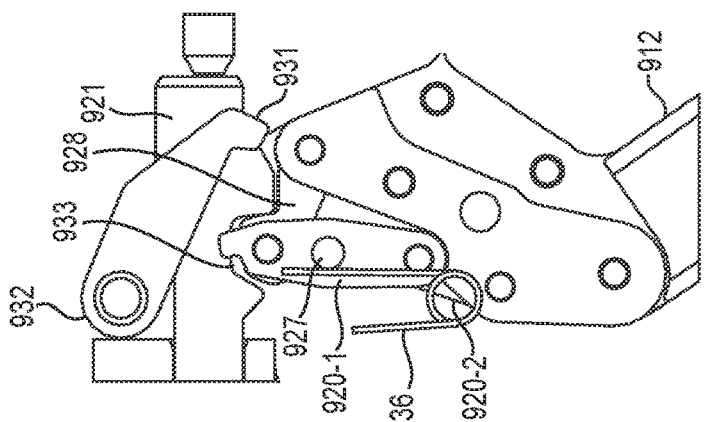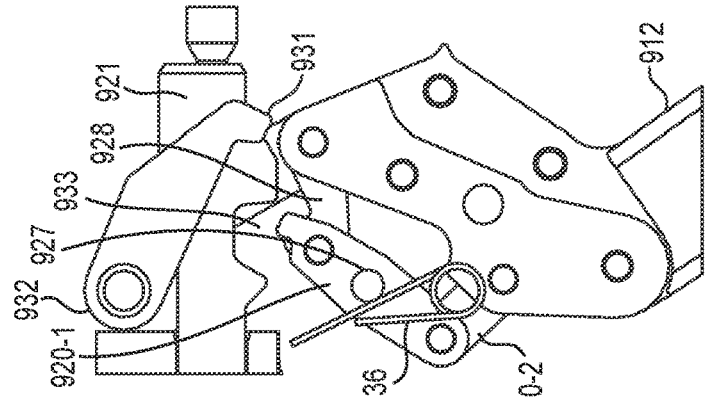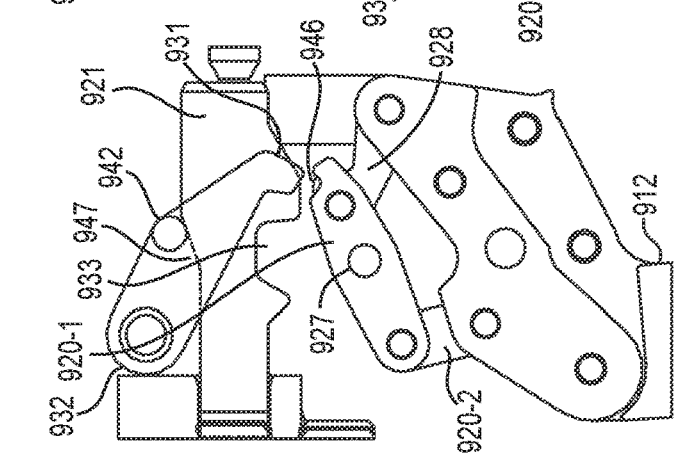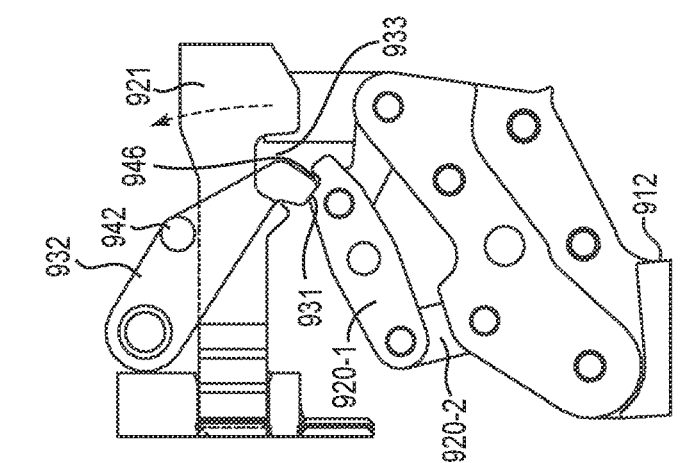

MOTORIZED SURGICAL HANDLE ASSEMBLY

RELATED APPLICATIONS

This application claims priority to U.S. provisional application 63/197,934 filed Jun. 7, 2021, the contents of which are hereby incorporated by reference herein for all purposes.

TECHNICAL FIELD

The present disclosure relates generally to surgical handle assemblies and to motor driven surgical devices.

BACKGROUND

A surgical handle assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. For example, a row of staples can have a linear length between 30 mm and 60 mm. A staple can be ejected by actuation of a movable handle member that is a part of the surgical handle assembly of the surgical stapler.

Some surgical staplers are equipped with an electric motor which can provide the power to clamp tissue, deliver staples, and provide power for other aspects of a surgical stapler.

BRIEF DESCRIPTION OF THE DRAWINGS

FIG. 3A is a schematic diagram of an embodiment of a movable handle in accordance with a number of embodiments of the present disclosure.

FIG. 3B is a schematic diagram of an exploded view of a movable handle in accordance with a number of embodiments of the present disclosure.

FIGS. 9A, 9B, 9C, and 9D are schematic diagrams of a reset mechanism for a movable handle in accordance with a number of embodiments of the present disclosure.

DETAILED DESCRIPTION

Figure 1:
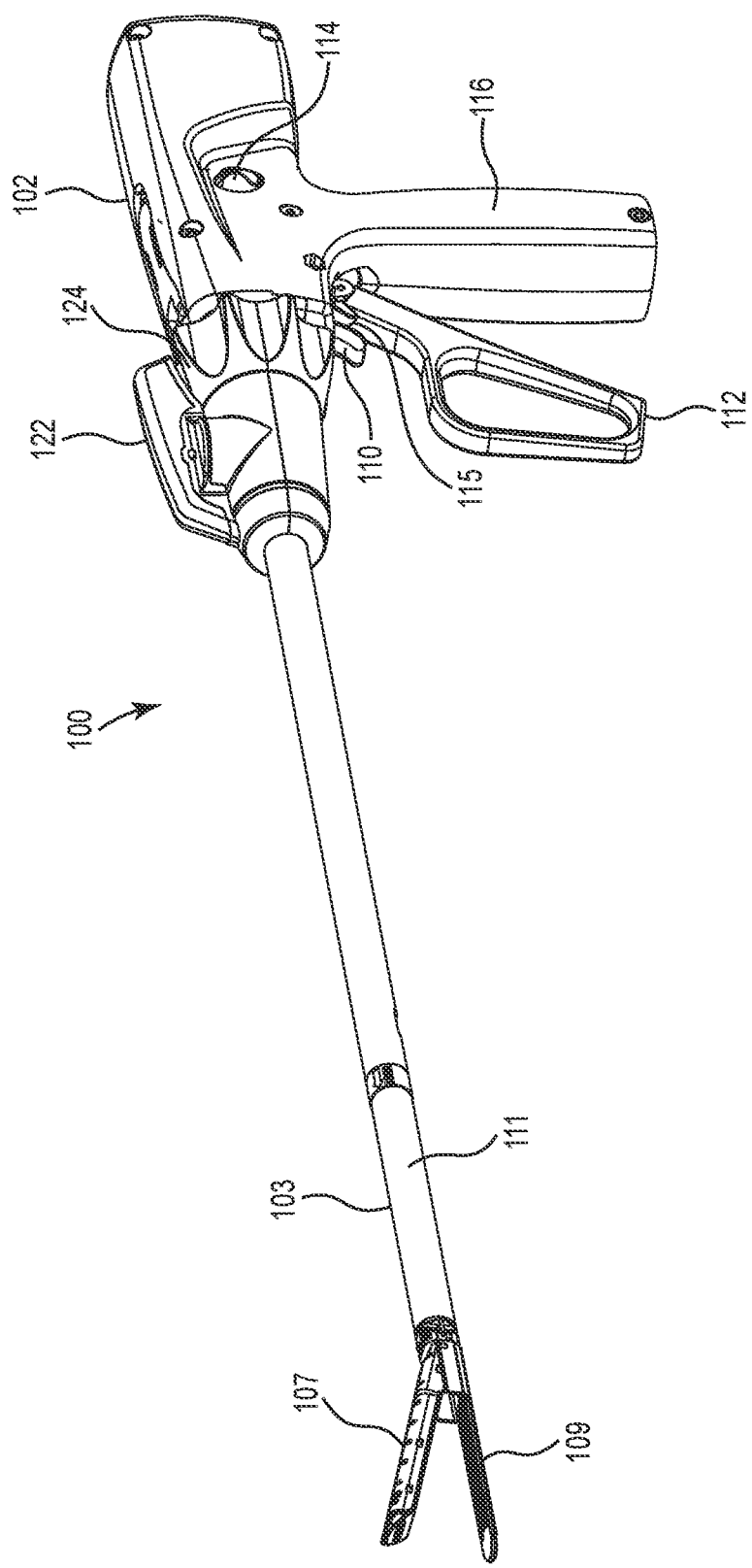
FIG. 1 is a schematic diagram of an apparatus including a motorized surgical handle assembly and a reloadable cartridge assembly in accordance with a number of embodiments of the present disclosure.

The present disclosure includes apparatuses for motorized or power surgical handle assemblies and surgical handles. An example apparatus includes a reloadable cartridge assembly and a motorized surgical handle assembly. The surgical handle includes a movable handle that allows for the clamping (e.g., grasping) and unclamping (e.g., ungrasping) of a reloadable cartridge assembly prior to delivering staples.

In a number of embodiments, the reloadable cartridge assembly can include a first elongated member and a second elongated member. The first elongated member and the second elongated member can sometimes be referred to as jaws. The jaws can be used to clamp and/or grasp tissue. One of the elongated members can house one or more staple cartridges. The other elongated member can have an anvil that can be used to form a staple when driven from the staple cartridge. In a number of embodiments, the motorized surgical handle assembly has a pawl that interfaces with a gear rack to move the gear rack proximally and distally to clamp (e.g., close) and/or unclamp (e.g., open) the jaws.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

It is to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of bosses) can refer to one or more bosses, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 102 may reference element "2" in FIG. 1, and a similar element may be referenced as 202 in FIG. 2. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a schematic diagram of an apparatus 100 including a motorized surgical handle assembly 102 and a reloadable cartridge assembly 103 in accordance with a number of embodiments of the present disclosure. In the example, the apparatus 100 can be a surgical stapler, for example.

As shown in the example of FIG. 1, the reloadable cartridge assembly 103, e.g., a disposable loading unit, can be releasably secured to a distal end of an elongated body of the motorized surgical handle assembly 102. In this example, the reloadable cartridge assembly 103 can include a cartridge shaft 111, a first elongated member 107 and a second elongated member 109 that can be used to clamp tissue. One of the elongated members can house one or more staple cartridges. The other elongated member can have an anvil that can be used to form a staple when driven from the staple cartridge. Apparatus 100 can receive reloadable cartridge assemblies having rows of staples. In a number of embodiments, third party reloadable cartridge and/or reloadable cartridge assemblies may be used with the motorized surgical handle assembly 102 and embodiments of motorized surgical handle assembly 102 may be configured to receive the same.

The motorized surgical handle assembly 102 can include a radial positioner 124, an articulation assembly activated by articulation knob 122, and non-movable handle (e.g., stationary handle) 116. The reloadable cartridge assembly 103 can be actuated using articulation knob 122 and/or radial positioner 124 to reach a stapling site. Radial positioner 124 rotates the reloadable cartridge assembly. Articulation knob 122 positions the elongated members 107 and 109 at a particular angle for stapling. The articulation knob 122 can be configured to actuate rotationally and the reloadable cartridge assembly 103 can rotate about an axis of a particular plane in response to the articulation knob 122 being actuated rotationally by a user. Movable handle 112 can be used to clamp and unclamp elongated members 107 and 109.

Power trigger 110 can be used to activate the electric motor to move the gear rack distally. Safety switch 115 may be used to allow power to flow to the electric motor and/or block the power trigger 110 from being activated. Reverse (e.g., retract) button 114 can be used to activate the electric motor to move the gear rack proximally.

Figure 2:
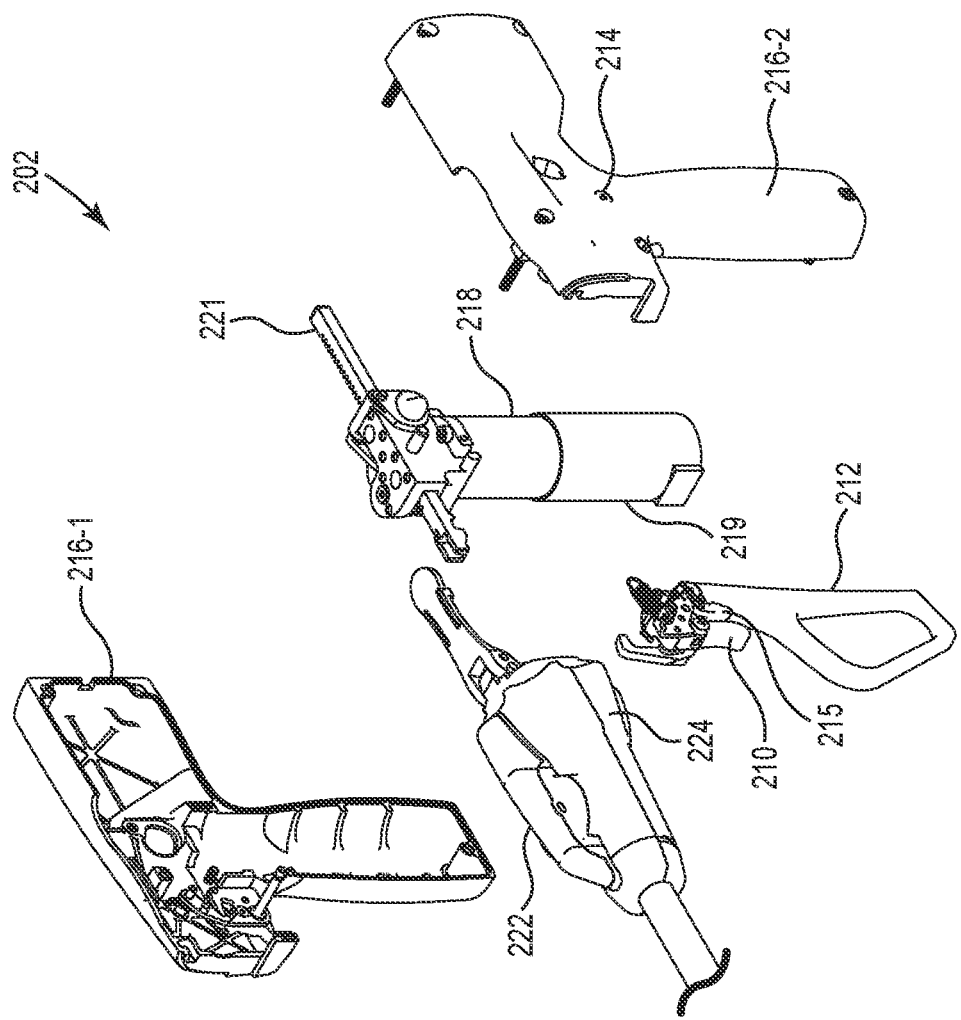
FIG. 2 is a schematic diagram of a motorized surgical handle assembly in accordance with a number of embodiments of the present disclosure.

FIG. 2 is a schematic diagram of a motorized surgical handle assembly 202 in accordance with a number of embodiments of the present disclosure. A distal portion of the motorized surgical handle assembly 202 can include the articulation knob 222 and radial positioner 224. Not shown is a driveshaft that cooperates with gear rack 221 to effect movement for a reloadable cartridge assembly (e.g., reloadable cartridge assembly 103 in FIG. 1). FIG. 2 illustrates a first handle half 216-1 and a second handle half 216-2 which provide a non-movable handle for the user of the device and houses a drive train 218. The first handle half 216-1 and/or the second handle half 216-2 may also include components that are used in the clamping and/or unclamping of the jaws. In some embodiments, drive train 218 can include a number of gears, not shown, and/or a power source such as a battery and/or an electric motor 219. In other embodiments, drive train 218 can include an electric motor and a number of gears and a battery can be located elsewhere such as between the first handle half 216-1 and the second handle half 216-2. In some embodiments the handle can include a power cord such that the electric motor can be powered by AC or DC current supplied from outside the device. The gear rack 221 can interact with the drive train 218 and a drive shaft, not shown, can be coupled to a distal end of the gear rack 221. Power trigger 210 and/or reverse button 214 can be used to activate the drive train 218, movable handle 212 can be used to clamp and unclamp the elongated members, and safety switch 215 can allow power to flow to the electric motor 219 and/or block the power trigger 210 from being activated.

FIG. 3A is a schematic diagram of an embodiment of a movable handle 312 in accordance with a number of embodiments of the present disclosure. The movable handle 312 can include a first side plate 326-1, a second side plate 326-2, a first linkage 320-1, a second linkage 320-2, a pawl 328, a disengagement pin 327, and a linkage spring 329.

FIG. 3B is a schematic diagram of an exploded view of a movable handle 312 in accordance with a number of embodiments of the present disclosure. The movable handle 312 can include a first side plate 326-1, a second side plate 326-2, a first linkage 320-1, a second linkage 320-2, a pawl 328, a disengagement pin 327, and a linkage spring 329.

Figure 4:
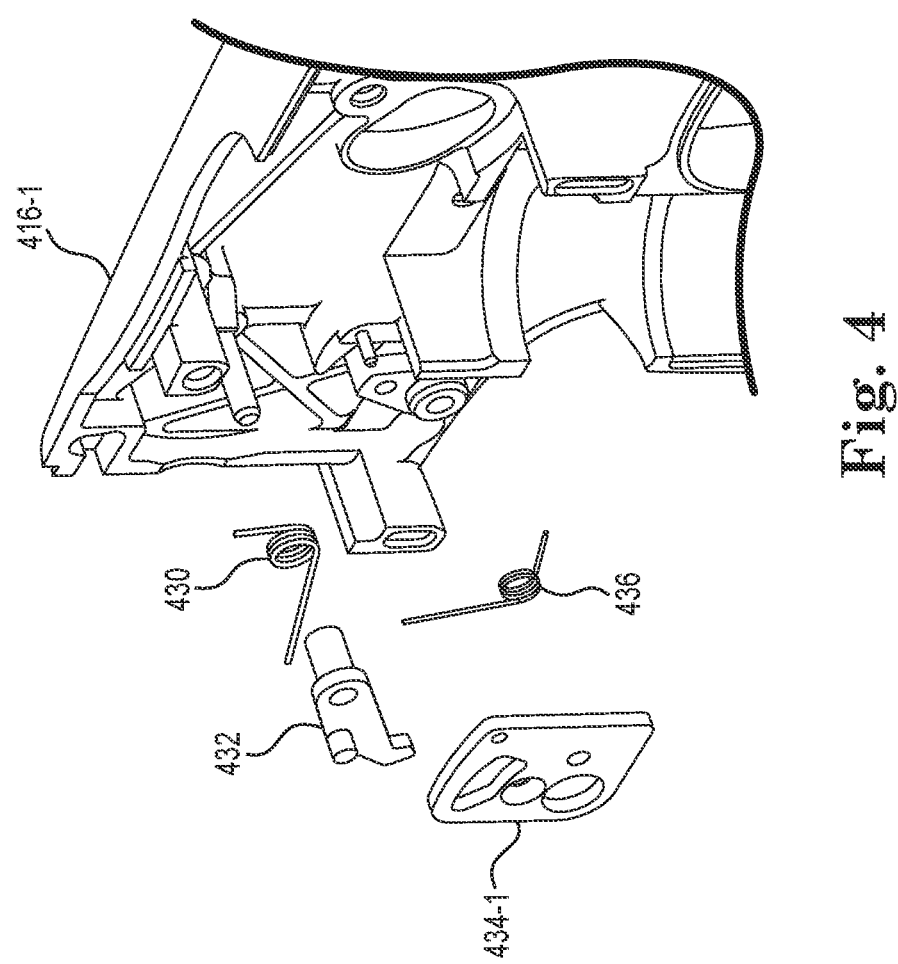
FIG. 4 is a schematic diagram of a first handle half in accordance with a number of embodiments of the present disclosure.

FIG. 4 is a schematic diagram of a first handle half 416-1 in accordance with a number of embodiments of the present disclosure. The first handle half 416-1 can include and/or be coupled to a movable handle lock spring 430, a clamp lock 432, a first disengagement insert 434-1, and a reset spring 436.

Figure 5:
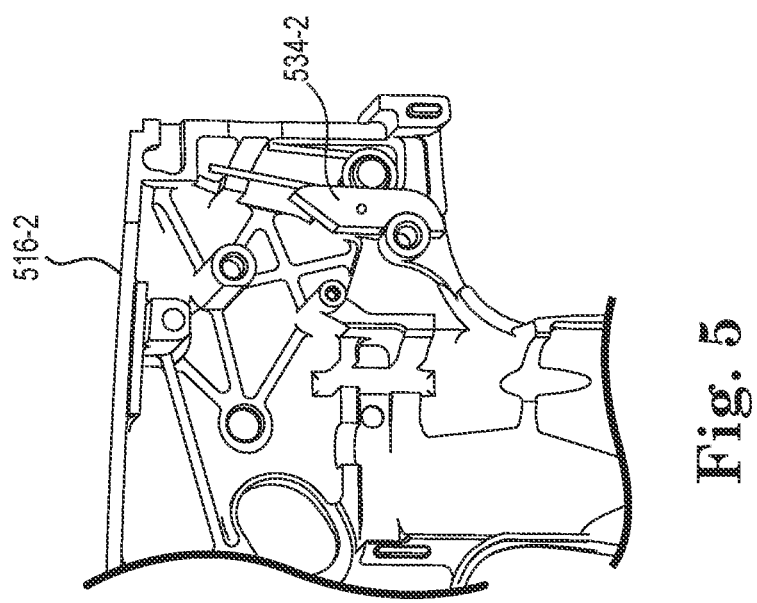
FIG. 5 is a schematic diagram of a second handle half in accordance with a number of embodiments of the present disclosure.

FIG. 5 is a schematic diagram of a second handle half 516-2 in accordance with a number of embodiments of the present disclosure. The second handle half 516-2 can include a second disengagement insert 534-2.

Figure 6C:
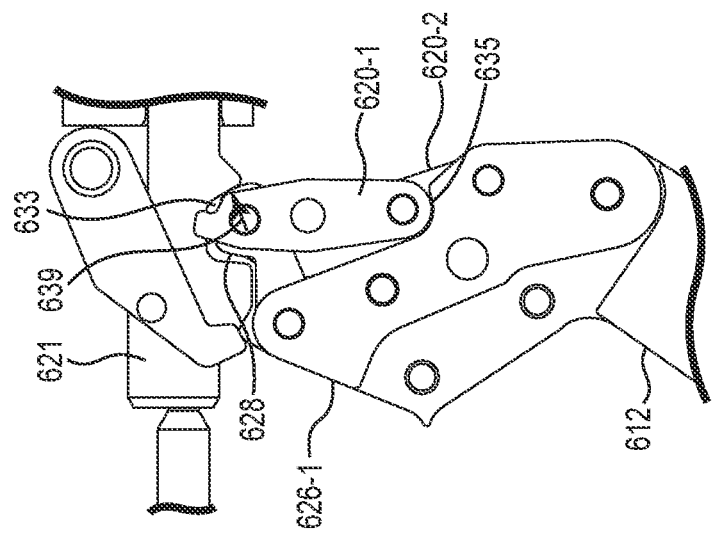
FIGS. 6A, 6B, and 6C are schematic diagrams of a mechanism for grasping and ungrasping a reloadable cartridge assembly in accordance with a number of embodiments of the present disclosure.
Figure 6B:
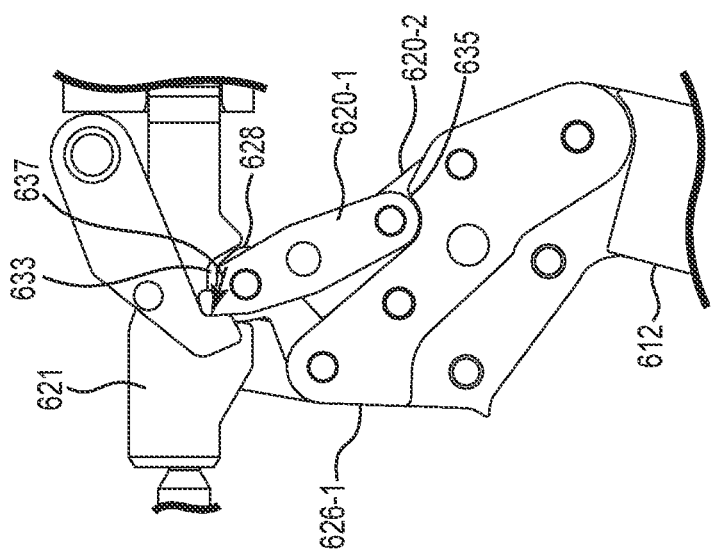
Figure 6A:
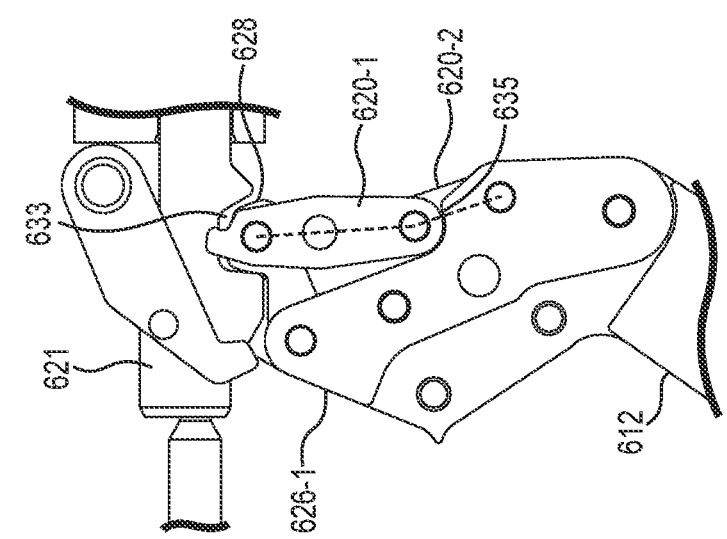

FIGS. 6A, 6B, and 6C are schematic diagrams of a mechanism for grasping and ungrasping a reloadable cartridge assembly (e.g., reloadable cartridge assembly 103 in FIG. 1) in accordance with a number of embodiments of the present disclosure. FIG. 6A illustrates an example of the movable handle 612 in a clamping state. In this view, pawl 628 is in gear rack notch 633 of gear rack 621. A first linkage 620-1 and a second linkage 620-2 can be relatively aligned and positioned adjacent to side plate 626-1. While the description uses the phrase 'relatively aligned,' the alignment is not critical. In the state shown in FIGS. 6A, 6B, and 6C, as movable handle 612 is moved proximally, pressure is exerted through the second linkage 620-2 and through the first linkage 620-1 to keep pawl 628 in gear rack notch 633. Also as shown, a pivot point junction 635 between the second linkage 620-2 and the first linkage 620-1 is pressing against movable handle 612. As the first linkage 620-1 and the second linkage 620-2 cannot move, the force is transmitted to the pawl 628. Also, as shown in FIG. 3A, linkage spring 329 is attached at one end to a lower attachment point of the second linkage 320-2 and at the other end to disengagement pin 327. The force of linkage spring 329 will attempt to move the first linkage 320-1 and the second linkage 320-2 out of alignment. Thus, when the first linkage 620-1 and the second linkage 620-2 are as shown in FIG. 6A, the first linkage 620-1 and/or the second linkage 620-2 can stay in a slightly over-center position as they try to overcome the force of the linkage spring (e.g., linkage spring 326 in FIG. 3A) to go over-center in the other direction. At many places in this disclosure, components are shown as being separate. The inventions disclosed here also cover embodiments where multiple components are integrated together into a single component.

In FIG. 6B, as a user actuates movable handle 612 proximally, pawl 628 pushes on the distal end of gear rack notch 633, as shown by arrow 637, moving gear rack 621 in a distal direction. This distal movement moves a drive assembly including the gear rack 621, a drive shaft, not shown, of a motorized surgical handle assembly (e.g., motorized surgical handle assembly 102 and 202 in FIG. 1 and FIG. 2, respectively), and a blade shaft, not shown, of a reloadable cartridge assembly (e.g., reloadable cartridge assembly 103 in FIG. 1) distally. In some embodiments, the distal end of the drive assembly comprises an I-beam. As the I-beam moves distally, the top and bottom sections of the I-beam will force elongated members (e.g., elongated members 107 and 109 in FIG. 1) to move toward each other in a clamping motion.

In FIG. 6C, as a user actuates movable handle 612 distally, pawl 628 pushes on the proximal end of gear rack notch 633, as shown by arrow 639, moving gear rack 621 in a proximal direction. This proximal movement moves the entire drive assembly including a drive shaft, not shown, of a surgical handle assembly (e.g., motorized surgical handle assembly 102 and 202 in FIG. 1 and FIG. 2, respectively), a blade shaft, not shown, of a reloadable cartridge assembly (e.g., reloadable cartridge assembly 103 in FIG. 1), and an I-beam, not shown, proximally. In some embodiments, as the I-beam moves proximally, the top and bottom sections of the I-beam will move away from interacting with elongated members (e.g., elongated members 107 and 109 in FIG. 1) which will allow the elongated members to move away from each other in an opening or unclamping motion.

Figure 7B:
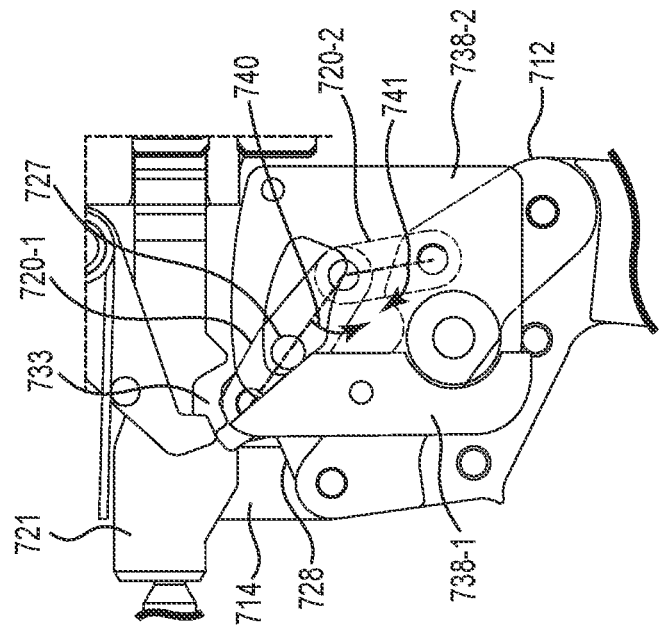
FIGS. 7A and 7B are schematic diagrams of a disengagement mechanism in accordance with a number of embodiments of the present disclosure.
Figure 7A:
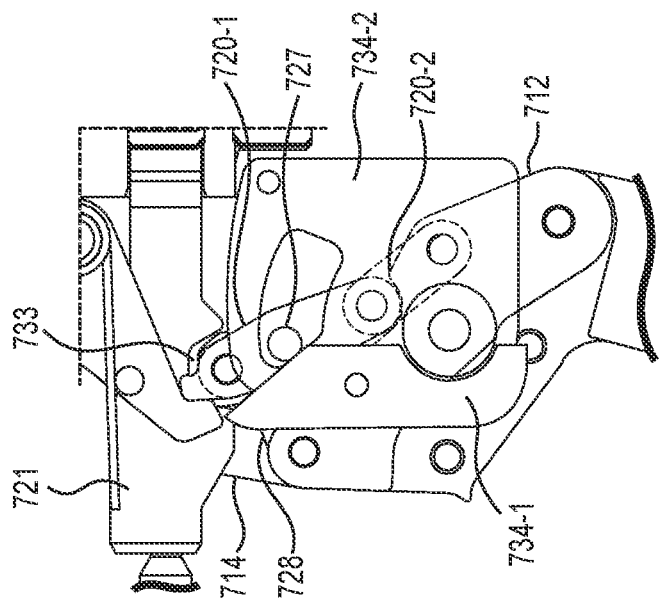

FIGS. 7A and 7B are schematic diagrams of a disengagement mechanism in accordance with a number of embodiments of the present disclosure. When the user has satisfactorily clamped the elongated members (e.g., elongated members 107 and 109 in FIG. 1) and they are placed in the desired position, further proximal movement of movable handle 712 will rotate pawl 728 out of gear rack notch 733. As seen in FIG. 7A, further proximal movement of movable handle 712 will cause disengagement pin 727 to contact a first disengagement insert 734-1 and a second disengagement insert 734-2. This contact will force the bottom of a first linkage 720-1 and a top of second linkage 720-2 to move away from movable handle 712. Arrows 740 and 741, as illustrated in FIG. 7B, show the middle of the first linkage 720-1 and the middle of the second linkage 720-2 moving toward each other. This movement pulls pawl 728 away from and out of gear rack notch 733 in gear rack 721. When movable handle 712 is in the locked position, the elongated members will stay in the clamped position. In some embodiments, the surgical handle assembly will not include a first insert 734-1 and the second insert 734-2 can cause the movement discussed earlier in this paragraph.

Figure 8B:
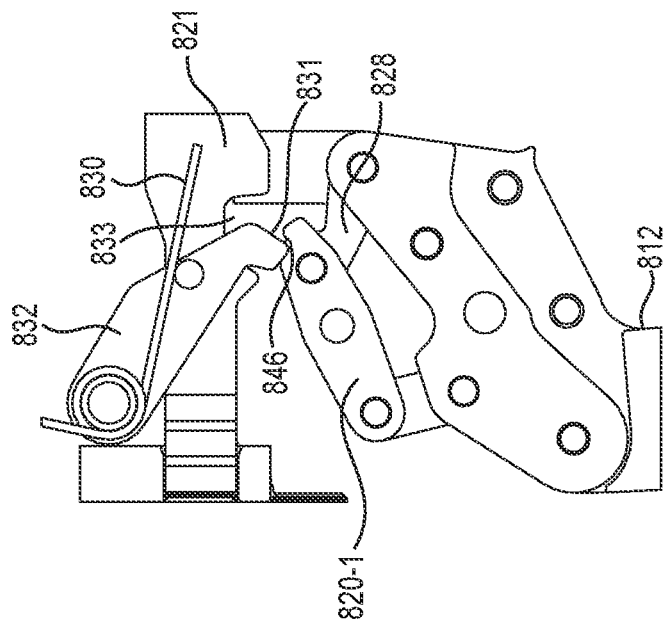
FIGS. 8A and 8B are schematic diagrams of a locking mechanism for a movable handle in accordance with a number of embodiments of the present disclosure.
Figure 8A:
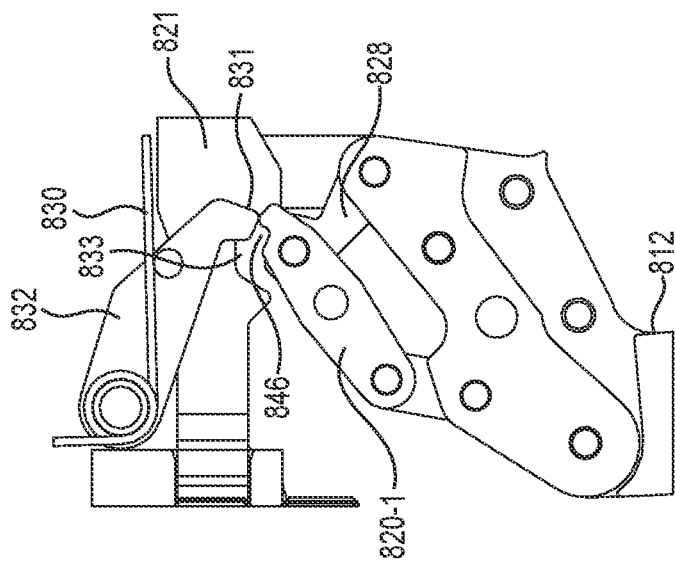

FIGS. 8A and 8B are schematic diagrams of a locking mechanism for a movable handle 812 in accordance with a number of embodiments of the present disclosure. As shown in FIG. 8A, movable handle lock spring 830 tensions clamp lock 832 against a first linkage 820-1. As the first linkage 820-1 is rotated, pawl 828 moves out of gear rack notch 833 and clamp lock 832 is rotated toward the first linkage 820-1 until a part of clamp lock 832, protrusion 831, is positioned in locking notch 846 of the first linkage 820-1. This is shown in FIG. 8B. The rotation of the pawl 828 and first linkage 820-1 is stopped by contact between the pawl 828 and the movable handle 812. The movable handle 812 is now locked in the proximal position. In this position, none of the components of the clamping/unclamping mechanism will interfere with the movement of gear rack 821 and the elongated members (e.g., elongated members 107 and 109 in FIG. 1) will stay in the clamped position.

Once the movable handle 812 is locked in the clamped position, the user may deliver some or all of the staples in a staple cartridge. This is accomplished by first activating a safety switch (e.g., safety switch 115 in FIG. 1) and then activating a power trigger (e.g., power trigger 210 in FIG. 2) which activates the drivetrain (e.g., drivetrain 218 in FIG. 2) to effect distal movement of the gear rack 821. Distal movement of a drive assembly causes an I-beam to advance through the elongated members and to deliver staples. The I-beam also comprises a cutting edge on the distal end so that stapled tissue is cut. At any time during a procedure, including immediately after locking the movable handle 812, after delivering some staples, or after delivering all the staples, a user may desire to unclamp the elongated members and/or retract the I-beam. To do this, the user activates reverse or retract button (e.g., retract button 114 in FIG. 1). The activation of the retract button causes a drivetrain (e.g., drivetrain 218 in FIG. 2) to drive gear rack 821 in a proximal direction moving the I-beam away from the elongated members, allowing the elongated members to open or unclamp. At this stage the movable handle 812 is allowed to spring to its distal position. Now, the user can either clamp the elongated members or replace the reloadable cartridge.

FIGS. 9A, 9B, 9C, and 9D are schematic diagrams of a reset mechanism for a movable handle 912 in accordance with a number of embodiments of the present disclosure with 9A and 9B showing the unlocking of the movable handle 912 and 9C and 9D showing the resetting of pawl 928 back into gear rack notch 933 as the handle opens. FIG. 9A shows cam lock 932 positioned within locking notch 946 of first linkage 920-1.

As shown in FIG. 9B, when a user activates retract button (e.g., retract button 114 in FIG. 1) causing a drivetrain to move a gear rack 921 in a proximal direction, lock cam 942, positioned on clamp lock 932, will interact with cam surface 947 of gear rack 921 when the gear rack 921 is almost fully retracted. This interaction will cause clamp lock 932 and protrusion 931 to rotate out of locking notch 946 of a first linkage 920-1 allowing the movable handle 912 to move distally. Although not illustrated, in a number of embodiments, the lock cam 942 can be positioned on gear rack 921 and can interact with a cam surface of clamp lock 932 to cause clamp lock 932 and protrusion 931 to rotate out of locking notch 946 allowing the movable handle 912 to move distally.

As shown in FIG. 9C, after movable handle 912 has moved in the distal direction, reset spring 936 exerts force on disengagement pin 927 which causes disengagement pin 927 to move toward movable handle 912 and pawl 928 into gear rack notch 933. In some examples, a cam surface on one or both of the handle halves (e.g., handle halves 216-1 and 216-2 in FIG. 2) can be used instead of or in tandem with the reset spring 936. For example, the disengagement pin can contact the cam surface and the cam surface can push the disengagement pin up as the movable handle 912 continues to open.

FIG. 9D shows the assembly after being reset. Now, pawl 928 is positioned in gear rack notch 933 of gear rack 921 and a first linkage 920-1 and a second linkage 920-2 are relatively aligned and slightly over-center. At this position, a user can either clamp elongated members (e.g., elongated members 107 and 109 in FIG. 1) or can change a reloadable cartridge.

Figure 10A:
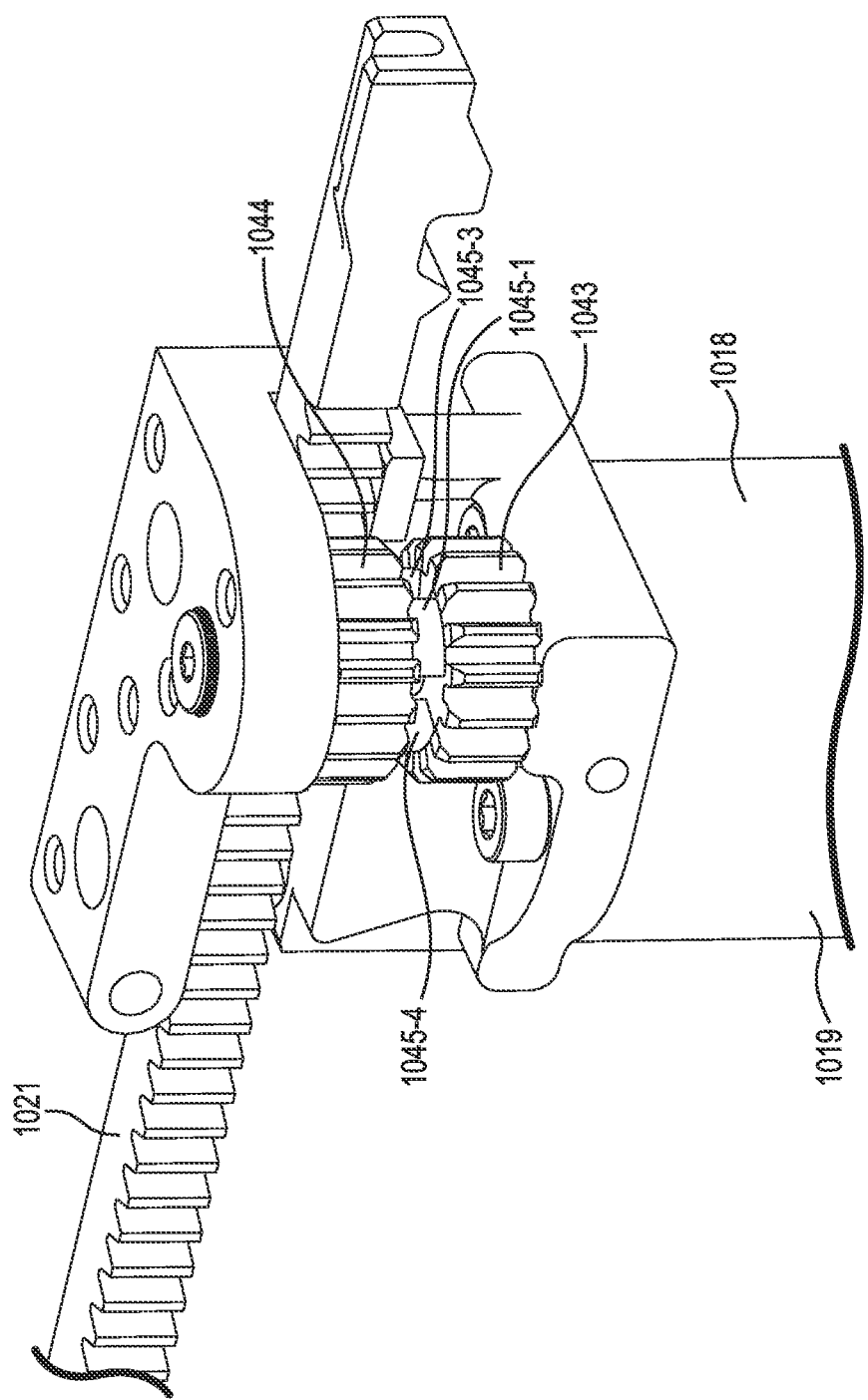
FIGS. 10A and 10B are schematic diagrams of a drive train in accordance with a number of embodiments of the present invention.
Figure 10B:
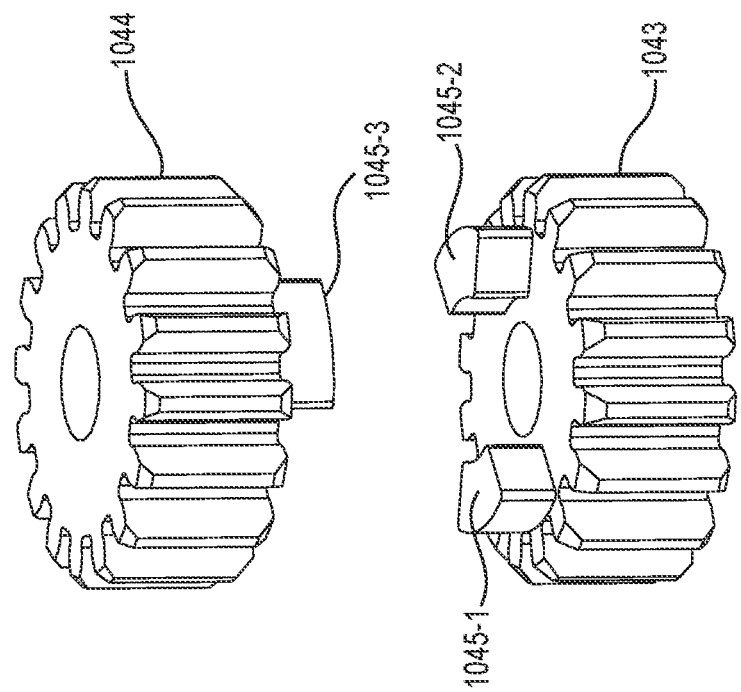

FIGS. 10A and 10B are schematic diagrams of a drive train 1018 in accordance with a number of embodiments of the present invention. Near the top of drive train 1018 is a gear system that includes driving gear 1043 and driven gear 1044. The electric motor 1019 rotates driving gear 1043 (either directly or through one or more other gears (not shown)) through the teeth on its circumferential surface and, through the interaction of bosses 1045-1 and/or 1045-2 with bosses 1045-3 and/or 1045-4, driving gear 1043 rotates driven gear 1044. Driven gear 1044 drives gear rack 1021 through its teeth on its circumferential surface. In some embodiments this will be referred to as a rack and pinion system. The rack, or gear rack 1021, moves in response to pinion or driven gear 1044 rotation as the cogs or teeth of driven gear 1044 interact with the cogs or teeth of gear rack 1021. In some embodiments, driven gear 1044 is associated with gear rack 1021 such that rotation of driven gear 1044 causes linear movement of gear rack 1021.

Shown in FIG. 10B are two bosses 1045-1 and 1045-2 positioned on top of driving gear 1043. Driven gear 1044 also has two bosses with boss 1045-3 and 1045-4 shown in the FIG. 10A. As electric motor 1019 rotates driving gear 1043, it will rotate until bosses 1045-1 and/or 1045-2 touch bosses 1045-3 and/or 1045-4. Further rotation of driving gear 1043 will cause rotation of driven gear 1044 and movement of gear rack 1021. The spacing between each of the bosses 1045-1, 1045-2, 1045-3, and 1045-4 allow for an amount of 'play' in the drive train system. Either driving gear 1043 or driven gear 1044 can rotate an amount without causing rotation of the other gear. The amount of play can be controlled by changing the width in the circumferential direction of the gears 1043 and 1044 of the bosses 1045-1, 1045-2, 1045-3, and 1045-4. Narrower bosses 1045-1, 1045-2, 1045-3, and 1045-4 will allow for more movement or play than wider bosses 1045-1, 1045-2, 1045-3, and 1045-4. While two bosses are shown on each gear, one or more bosses 1045-1, 1045-2, 1045-3, and 1045-4 could be used on one or both gears 1043 and 1044. As discussed herein, when movable handle (e.g., movable handle 112 in FIG. 1) is moved proximally and distally to clamp and unclamp elongated members (e.g., elongated members 107 and 109 in FIG. 1), this play in the system allows the gear rack 1021 and driven gear 1044 to move an amount sufficient to clamp or unclamp the elongated members without causing rotation of driving gear 1043. With some systems, rotation of driving gear 1043 will be very difficult due to the high gear reduction in electric motor 1019. In some embodiments, electric motor 1019 is described as being connected to driving gear 1043. In some embodiments, there is an additional gear system, not shown, in between the output of the electric motor 1019, generally a rotating shaft, and driving gear 1043. In some embodiments, gears 1043 and 1044 are identical, they are just mounted in a mirror image fashion. While gears 1043 and 1044 are shown with bosses 1045-1, 1045-2, 1045-3, and 1045-4 that extend away from a surface of the gears 1043 and 1044, in some embodiments a first gear of the gears 1043 or 1044 can have at least one boss of one or more bosses 1045-1, 1045-2, 1045-3, and 1045-4 that extends away from the surface while a second gear of the gears 1044 or 1043 can have a depression in the surface that will interact with the at least one raised boss of the first gear. In some embodiments, the width of the bosses can be balanced as thinner cogs enable larger potential movement of one gear relative to the other gear without needing to overcome the force of drive train 1018 but a boss that is too thin could be sheared off. In some embodiments, the number of and thickness of bosses (or depression(s)) will dictate the relative movement of a first gear relative to a second gear before the second gear will begin to move, but in all embodiments this distance, or amount of 'play,' will be less than 360°. In embodiments where each gear has only one boss, the amount of play may be between 250° to 290°. In embodiments where each gear has two bosses, the play may be in the range of 60° to 100° or, in some embodiments, about 70°.

Figure 11:
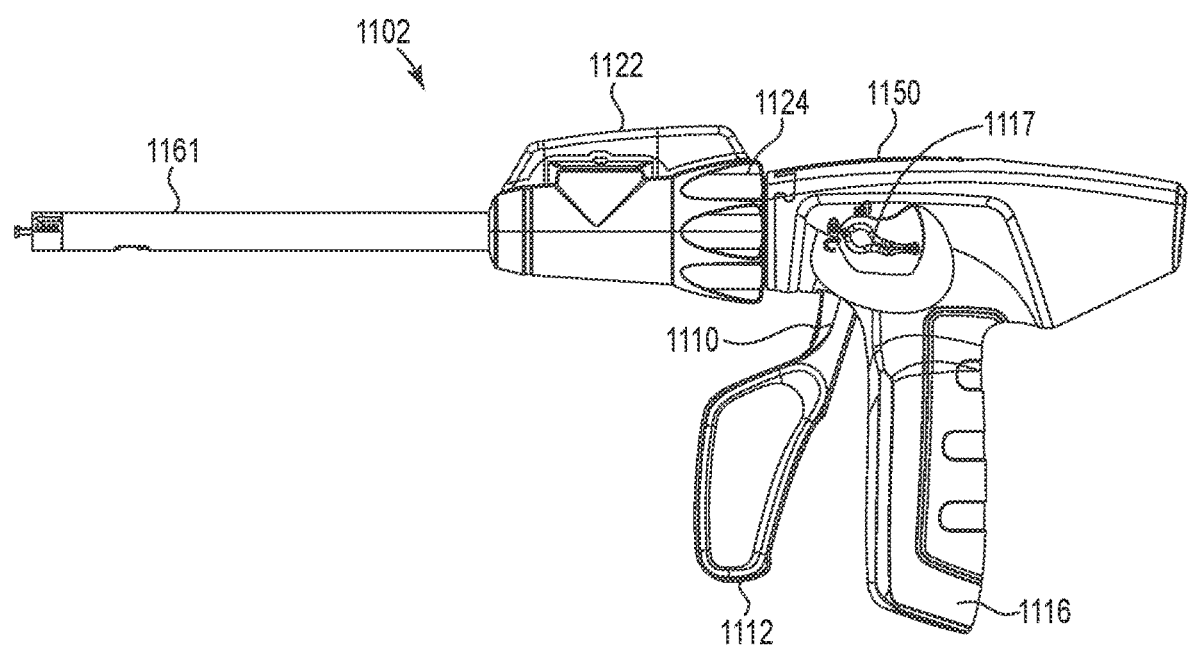
FIG. 11 is a schematic of a motorized surgical handle assembly in accordance with a number of embodiments of the present disclosure

FIG. 11 is a schematic diagram of a motorized surgical handle assembly 1102 in accordance with a number of embodiments of the present disclosure. In use, motorized surgical handle assembly 1102 can be attached to reloadable cartridge assembly (e.g., reloadable cartridge assembly 103 in FIG. 1). As shown in the example of FIG. 11, the motorized surgical handle assembly 1102 can include a radial positioner 1124, an articulation assembly activated by articulation knob 1122, non-movable handle 1116, outer shaft 1161, and manual retraction or bailout handle 1150. Movable handle 1112 can be used to clamp and unclamp elongated members (e.g., elongated members 107 and 109 in FIG. 1). Power trigger 1110 can be used to activate the electric motor to move the gear rack (e.g., gear rack 1021 in FIG. 10A) distally.

Selector lever 1117 can include a number of settings, which can include a locked position (e.g., safe), an unlocked position (e.g., fire), and a reverse position. While the selector lever 1117 is in the locked position, movable handle 1112 may be used to clamp and unclamp the jaws but power trigger 1110 is electrically deactivated. When the selector lever 1117 is in the unlocked position, power trigger 1110 may be used to allow power to flow to an electric motor. As will be discussed later, movable handle 1112 needs to be in a proximal position before the selector lever 1117 can be moved from the locked position to the unlocked position. When set to the reverse (e.g., retract) position which, in some embodiments, is a momentary position, selector lever 1117 will cause the electric motor to be activated to move the gear rack proximally.

Figure 12:
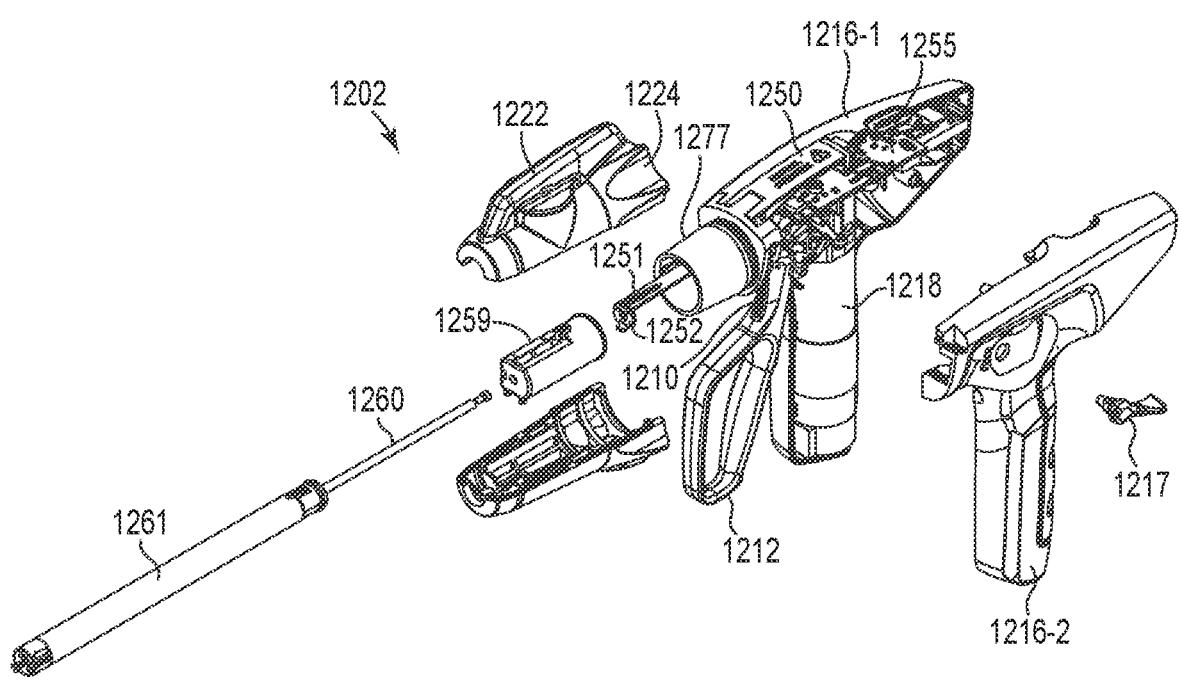
FIG. 12 is a schematic diagram of an exploded view of a motorized surgical handle assembly in accordance with a number of embodiments of the present disclosure.

FIG. 12 is a schematic diagram of an exploded view of a motorized surgical handle assembly 1202 in accordance with a number of embodiments of the present disclosure. A distal portion of the motorized surgical handle assembly 1202 can include the articulation knob 1222 and radial positioner 1224. Drive shaft (e.g., drive rod) 1260 cooperates with the gear rack (e.g., gear rack 1021 in FIG. 10A) to effect movement for a reloadable cartridge assembly (e.g., reloadable cartridge assembly 103 in FIG. 1).

FIG. 12 illustrates a second handle half 1216-2 which, along with first handle half 1216-1, provides a non-movable handle (e.g., non-movable handle 1116 in FIG. 11) for the user of the motorized surgical handle assembly 1201, houses a drive train 1218, and encases the electrical and mechanical mechanisms. The first handle half 1216-1 and/or the second handle half 1216-2 may also include components that are used in the clamping and/or unclamping of the jaws.

In some embodiments, drive train 1218 can include a number of gears, not shown, and/or a power source such as a battery and/or an electric motor that can be battery powered or connected to an external power source, such as, an alternating current (AC) source. In other embodiments, drive train 1218 can include an electric motor, a number of gears, and/or a battery that can be located elsewhere, such as, between the first handle half 1216-1 and the second handle half 1216-2. A gear rack (e.g., gear rack 1021 in FIG. 10A) can interact with the drive train 1218 and a drive shaft 1260 can be coupled to a distal end of the gear rack.

Power trigger 1210 and selector lever 1217 can be used to activate the drive train 1218. Movable handle 1212 can be used to clamp and unclamp the elongated members, and selector lever 1217 can allow power to flow to the electric motor and/or block the power trigger 1210 from being activated. Also shown in FIG. 12 is outer shaft 1261, nose cone 1277, bailout handle 1250, circuit board 1255, articulation lock 1259, toggle plates 1252, and bailout bar 1251.

Figure 13:
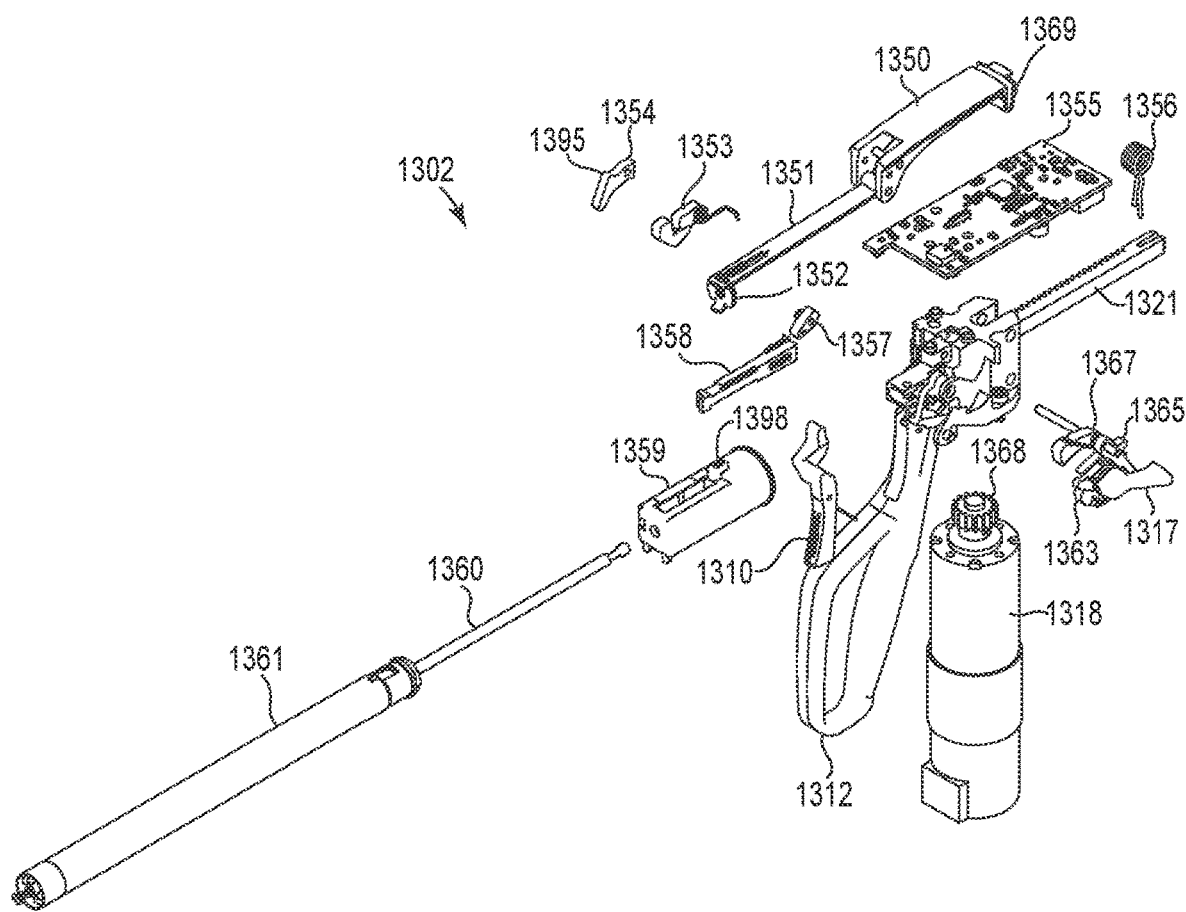
FIG. 13 is a schematic diagram of an exploded view of a motorized surgical handle assembly in accordance with a number of embodiments of the present disclosure.

FIG. 13 is a schematic diagram of an exploded view of a motorized surgical handle assembly 1302 in accordance with a number of embodiments of the present disclosure. Selector lever 1317 is non-rotationally fixed to selector cam 1363. When selector lever 1317 is rotated to the unlocked position, which can only happen when movable handle 1312 is moved to its most proximal position and the jaw assembly is closed, selector cam 1363 rotates and protrusion (e.g., protrusion 1785 in FIGS. 17B and 17C) activates a switch (e.g., switch 1683 in FIG. 16B) on circuit board 1355. When the switch is activated, energy is allowed to flow to drive train 1318.

When selector lever 1317 is rotated to the reverse position, selector cam 1363 rotates reverse cam 1365 and causes protrusion 1497 on reverse cam 1365 to activate reverse switch 1684 on circuit board 1355 and causes drive train 1318 to move in reverse to retract gear rack 1321 and drive shaft 1360. When activated, drive train 1318 causes gear 1368 to rotate. Gear 1368 is configured to cause driving gear (e.g., gear 1043 in FIGS. 10A and 10B) to rotate and move gear rack 1321. The proximal end of drive shaft 1360 extends through articulation lock 1359 and is connected to the distal end of gear rack 1321. A portion of drive shaft 1360 is housed within outer shaft 1361.

When gear rack 1321 is fully reversed, retraction spring 1356 will be compressed and a control system will experience a spike in current as the gear rack 1321 is positioned against retraction spring 1356 and other components of the motorized surgical handle assembly 1302. At this point drive train 1318 will change direction and rotate the driving gear to unload retraction spring 1356, which causes the gear rack 1321 to move in the distal direction a short distance, for example 0.5, 1, 1.2, or 2 mm. This forward movement unloads retraction spring 1356 and will position bosses (e.g., bosses 1045-1 and 1045-2 in FIG. 10B) of driving gear (e.g., driving gear 1043 in FIGS. 10A and 10B) between bosses (e.g., bosses 1045-3 and 1045-4 in FIG. 10A) of driven gear (e.g., driven gear 1044 in FIGS. 10A and 10B) so that the clamp and unclamp mechanism will work.

When movable handle 1312 is moved to the proximal most position the frictional force of friction cam 1353 and its associated spring on movable handle 1312 will hold movable handle 1312 in the proximal most position. A user/physician can open the jaws by moving the movable handle 1312 distally manually, by forcing the movable handle 1312 distally, or by using the reverse function of the selector lever 1317.

When the selector lever 1317 is rotated to the unlocked position, surface (e.g., surface 1788 in FIG. 17B) of selector cam 1363 will rotate against a locking protrusion (e.g., locking protrusion 1489 in FIG. 14) of movable handle 1312 and lock movable handle 1312 in the proximal position. After the gear rack 1321 begins to travel distally, locking cam 1367 will interact with a notch (e.g., notch 1490 in FIG. 14) of movable handle 1312 and lock movable handle 1312 in the proximal position.

When a reload unit, such as reloadable cartridge assembly 103 in FIG. 1, is attached to the distal end of the motorized surgical handle assembly 1302, a bar, not shown, connected to the distal end of articulation lock 1359 will move proximally and cause articulation lock 1359 to move proximally. Proximal movement of articulation lock 1359 moves bar 1358 which moves cam 1357 into contact with (e.g., closes) reload switch (e.g., reload switch 1682 in FIG. 16B) on circuit board 1355 which allows drive train 1318 to be activated. If there is no reloadable cartridge assembly attached to the motorized surgical handle assembly 1302, drive train 1318 cannot be activated.

Protrusion 1398 on articulation lock 1359 is configured to interact with an articulation mechanism of motorized surgical handle assembly 1302 such that articulation knob (e.g., articulation knob 1222 in FIG. 12) cannot be rotated if a reloadable cartridge assembly is not attached to the motorized surgical handle assembly 1302. When a reloadable cartridge assembly is attached, the movable handle 1312 is in the proximal most position, selector lever 1317 is switched to an unlocked position, and a user moves power trigger 1310 proximally, trigger 1310 pushes intermediate lever 1354, specifically protrusion 1395, into contact with a power switch (e.g., power switch 1681 in FIG. 16B) on circuit board 1355 causing the drive train 1318 to move gear rack 1321 in a distal direction.

Friction cam 1353 is configured to provide friction to movable handle 1312 so that the handle is less likely to move without a user moving it in a proximal or distal direction. Bailout handle 1350 includes u-shaped latch 1369. U-shaped latch 1369 is configured to interact with the first handle half (e.g., first handle half 1216-1 in FIG. 12) and the second handle half (e.g., second handle half 1216-2 in FIG. 12) to keep bailout handle 1350 secured in the down position. The bottom of the u-shaped latch 1369 interacts with switch (e.g., switch 1680 in FIG. 16A) on circuit board 1355. When the switch is closed (e.g., pressed), power is supplied to the circuit board 1355. When bailout handle 1350 is lifted and u-shaped latch 1369 is not in contact with switch 1680 (e.g., the switch is open), no power will flow to the circuit board 1355. Additional functions and uses of bailout handle 1350, bailout bar 1351, and toggle plates 1352 will be explained elsewhere.

Figure 14:
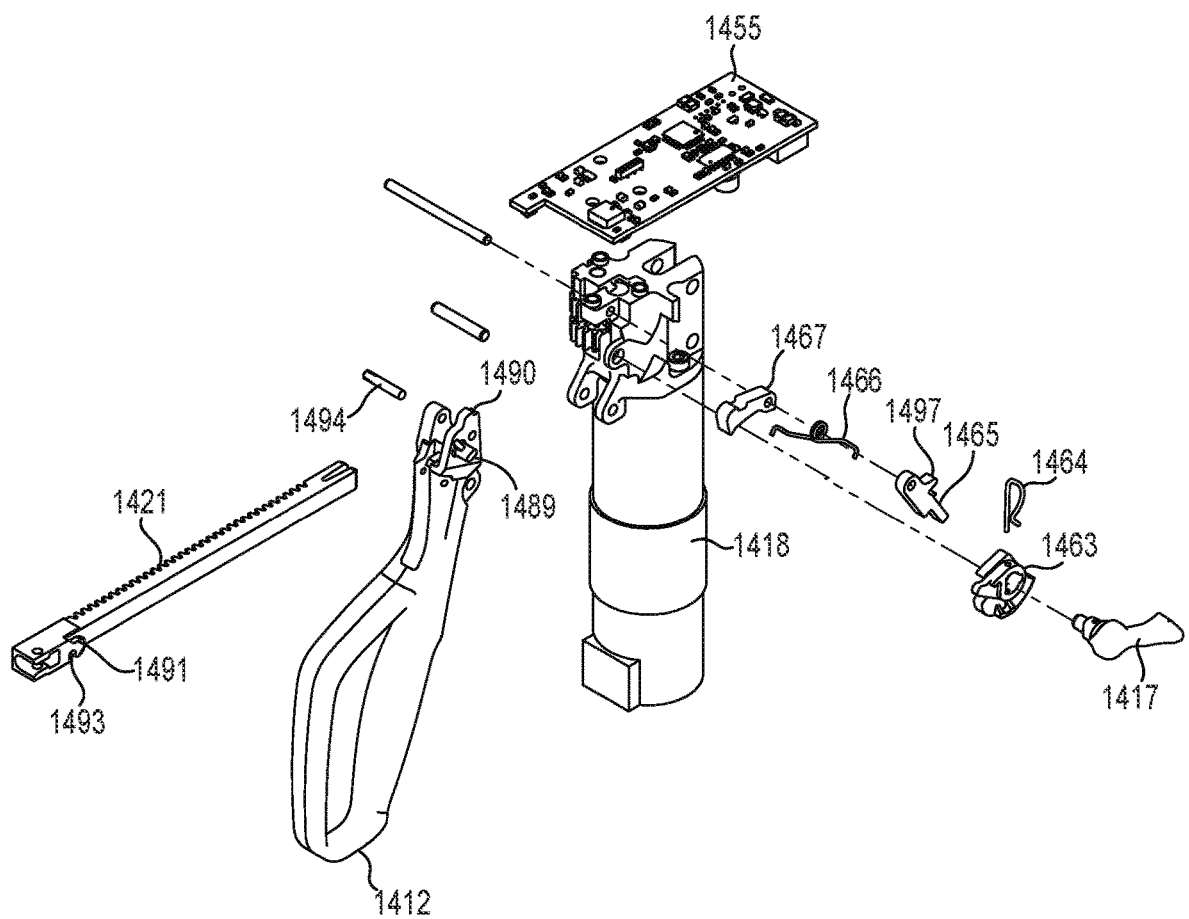
FIG. 14 is a schematic diagram of a part of a motorized surgical handle assembly in accordance with a number of embodiments of the present disclosure.

FIG. 14 is a schematic diagram of aspects of a selector lever 1417 of a motorized surgical handle assembly (e.g., motorized surgical handle assembly 1302 in FIG. 13) in accordance with a number of embodiments of the present disclosure. Selector lever 1417 is non-rotationally attached to selector cam 1463 by pin 1464. In some embodiments, selector lever 1417 and selector cam 1463 can be a single piece and pin 1464 will not be needed. When assembled, selector cam 1463 rotates with selector lever 1417. When selector lever 1417 is rotated to the unlocked position, protrusion (e.g., protrusion 1785 in FIGS. 17B and 17C on selector cam 1463 rotates into contact with (e.g., closes) switch (e.g., switch 1683 in FIG. 16B) on circuit board 1455 putting a movable handle 1412 into the ready to fire position.

When selector lever 1417 is rotated to a reverse position, reverse cam 1465 is rotated by selector cam 1463 so that protrusion 1497 moves into contact with (e.g., closes) reverse switch (e.g., reverse switch 1684 in FIG. 16B) on circuit board 1455 and causes drive train 1418 to move gear rack 1421 in a proximal direction. Spring 1466 is configured so that reverse cam 1465, selector cam 1463, and selector lever 1417 immediately move back to the locked position after the physician/user stops exerting force on selector lever 1417 after having turned selector lever 1417 to the reverse position.

Locking cam 1467 moves into contact with proximally positioned movable handle 1412 when selector lever 1417 is moved to the unlocked position and locks movable handle 1412 in the proximal most position after the gear rack 1421 has been advanced by drive train 1418. Also shown on movable handle 1412 is notch 1490, locking protrusion (e.g., projection) 1489 and, when assembled, rod (e.g., bar) 1494 spans the opening in the top of the handle. Shown on gear rack 1421 is protrusion (e.g., raised edge) 1491 and gear rack slot 1493.

When movable handle 1412 is moved to the proximal most position, the frictional force of friction cam (e.g., friction cam 1353 in FIG. 13) and its associated spring on movable handle 1412 will hold movable handle 1412 in the proximal most position. A user/physician can open the jaws by moving the movable handle 1412 distally manually, by forcing the movable handle 1412 distally, or by using the reverse function of the selector lever 1417.

Locking protrusion 1489 will prevent selector cam 1463 and selector lever 1417 from being rotated to the unlocked position if movable handle 1412 is not in the proximal most position. When movable handle 1412 is moved to its proximal most position and selector lever 1417 and selector cam 1463 are turned to the unlocked position, surface (e.g., surface 1788 in FIG. 17B) of selector cam 1463 will move into contact with locking protrusion 1489 and hold or lock movable handle 1412 in the clamped position.

When gear rack 1421 is in a proximal position, such that jaws can be clamped and unclamped, locking cam 1467 will be resting on protrusion 1491 on gear rack 1421 and prevented from moving into notch 1490 on the movable handle 1412. If a user/physician advances the gear rack 1421 distally, protrusion 1491 will also move distally and out of engagement with locking cam 1467. This will allow the distal tip of locking cam 1467 to move into notch 1490 and lock the movable handle 1412 in the proximal position. Locking cam 1467 will stay engaged with notch 1490 until gear rack 1421 is moved proximally and into a position where the clamp/unclamp of the jaws can be performed (e.g., a grasping position of the gear rack 1421) as protrusion 1491 will, at this point, force locking cam 1467 out of notch 1490.

FIGS. 15A, 15B, 15C, and 15D are schematic diagrams of a bailout mechanism for a motorized surgical handle assembly (e.g., motorized surgical handle assembly 1302 in FIG. 13) in accordance with a number of embodiments of the present disclosure. In the event that a surgical stapler, such as apparatus 100 in FIG. 1, malfunctions during use, the user needs a way to open the jaws, so that the jaws are no longer clamping tissue.

In a number of embodiments, a bailout mechanism is provided including a bailout handle 1550 pivotably connected to bailout bar (e.g., bailout bar 1351 in FIG. 13). A cam pin, not shown, extends through cam opening 1571 of bailout handle 1550 and is positioned in cam slot 1572. Bailout bar is rotationally connected to bailout handle 1550 at connection 1578. When fully assembled, distal upper hook 1576 is positioned within proximal upper hook 1575 and distal lower hook 1574 is positioned within proximal lower hook 1573. The distal hooks 1576 and 1574 are positioned on nose cone 1577 and the proximal hooks 1573 and 1575 are positioned on first and/or second handle halves 1516-1 and 1516-2. In some embodiments, there are two upper and two lower hook pairs.

When a user moves the proximal end of bailout handle 1550 up and away from the motorized surgical handle assembly, the cam pin will be forced in a downward direction as cam opening 1571 is positioned distal to the pivot point 1505 for bailout handle 1550. This downward force will put pressure on cam slot 1572 forcing first and second handle halves 1516-1 and 1516-2 in a downward direction. The downward movement of the first and second handle halves 1516-1 and 1516-2 will cause proximal lower hook 1573 to move away from distal lower hook 1574 and proximal upper hook 1575 to move away from distal upper hook 1576. At this point, a proximal casing of the motorized surgical handle assembly including the first and second handle halves 1516-1 and 1516-2 is no longer connected to a distal casing including a radial positioner (e.g., radial positioner 1224 in FIG. 12), an articulation knob (e.g., articulation knob 1222 in FIG. 12), an associated articulation assembly, an outer shaft (e.g., outer shaft 1261 in FIG. 12), and components of a reloadable cartridge assembly (e.g., reloadable cartridge assembly 103 in FIG. 1).

Figure 15A:
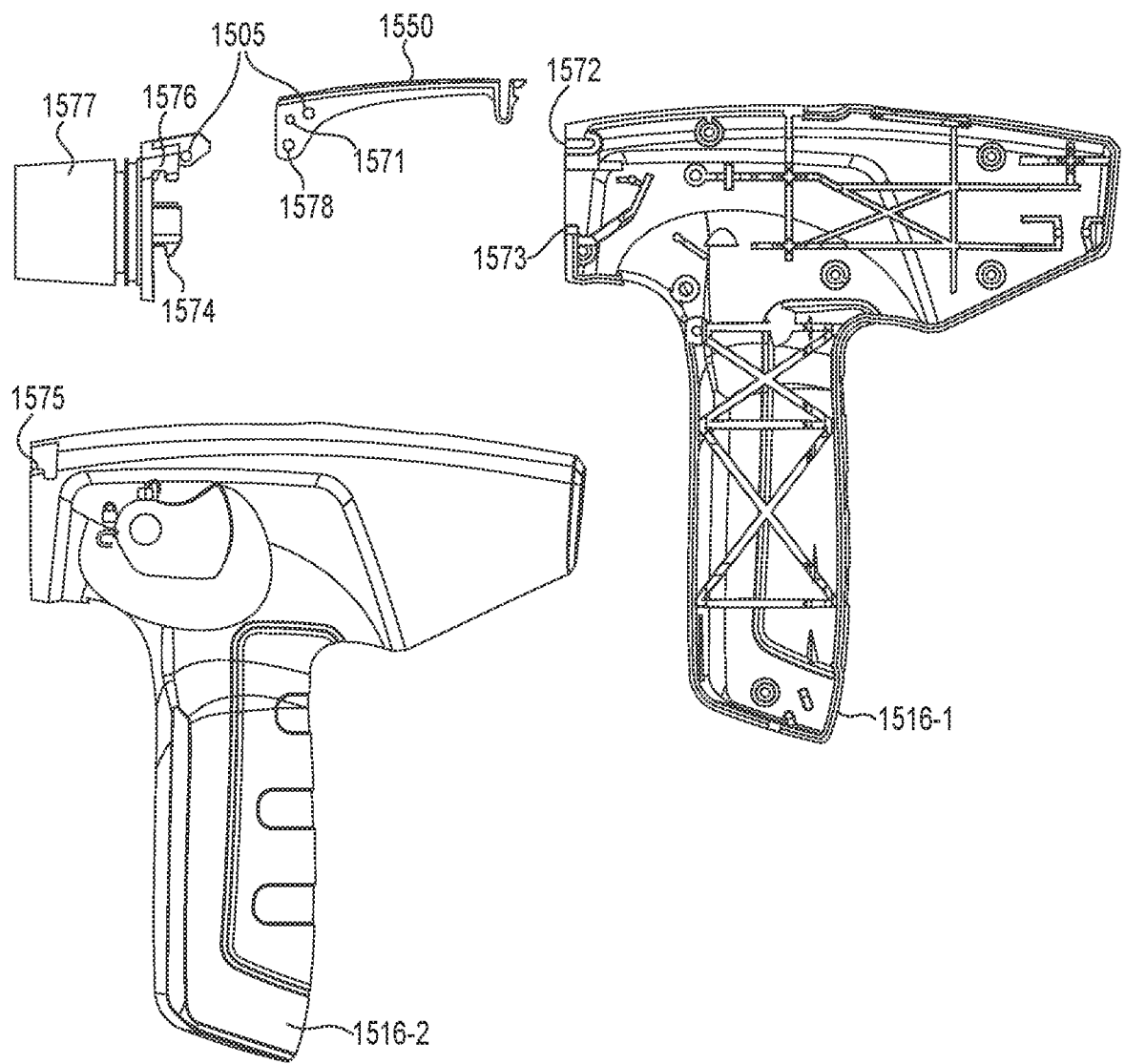
FIGS. 15A, 15B, 15C, and 15D are schematic diagrams of the bailout mechanism for a motorized surgical handle assembly in accordance with a number of embodiments of the present disclosure.
Figure 15B:
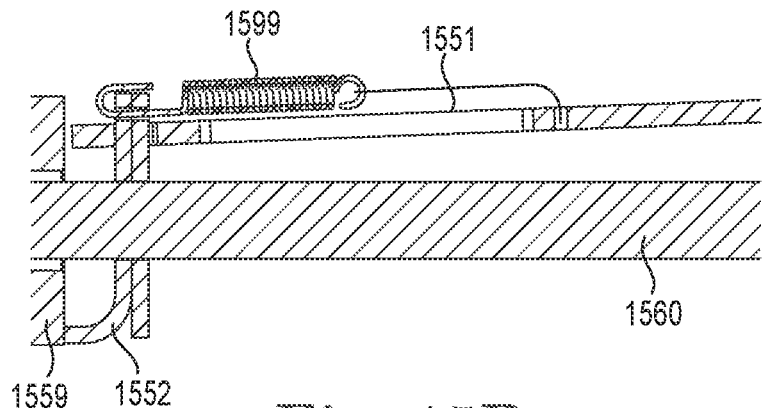

Prior to moving bailout handle 1550, the bailout mechanism is as shown in FIG. 15B. With a reloadable cartridge assembly attached, articulation lock 1559 has been moved proximally against a distal facing protrusion on the distal most toggle plate 1552 and moves toggle plates 1552 into a perpendicular or relatively perpendicular relationship with drive shaft 1560. In this relationship, the toggle plates 1552 do not interfere with the movement of drive shaft 1560. In this embodiment, two toggle plates 1552 are shown. Any number such as 1, 2, 3, 4, or more toggle plates 1552 can be used as long as the distal most toggle plate 1552 has a distal facing protrusion. In some embodiments, the articulation lock 1559 or another component could have a protrusion that would bring a cylindrical toggle plate(s) 1552 into the perpendicular or relatively perpendicular relationship with the drive shaft 1560 and the distal facing protrusion will not be needed.

Figure 15C:
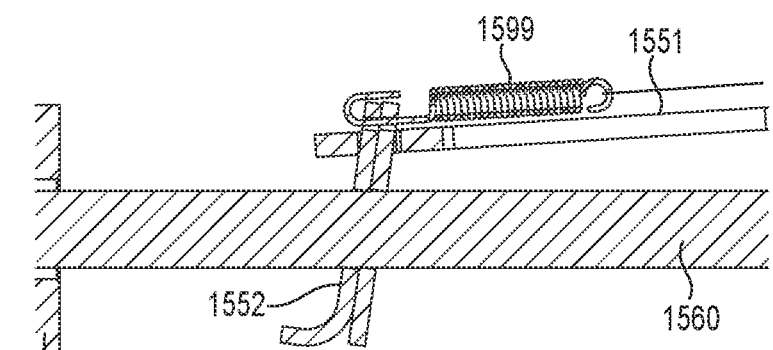

As the user rotates bailout handle 1550, bailout bar is moved proximally and toggle plates 1552 are moved out of contact with articulation lock 1559. As shown in FIG. 15C, once the toggle plates 1552 are out of contact with articulation lock 1559 and also due to the force of bailout spring 1599, the top of toggle plates 1552 will move proximally causing the toggle plates 1552 to come into contact with and bite on drive shaft 1560. As the bailout handle 1550 is rotated upward, distal outer casing is forced distal relative to the drive shaft 1560 as the bailout handle 1550 is attached to the distal outer casing.

Likely, as the surgical stapler will be in use when the bailout mechanism is used, this distal motion of the distal outer casing will cause drive shaft 1560 and the partial motorized surgical handle assembly to move proximally as the jaws will be clamped on tissue. During this movement, neither the drive shaft 1560 or the gear rack (e.g., gear rack 1424 in FIG. 14) will move relative to the first and second handle halves 1516-1 and 1516-2, a movable handle (e.g., movable handle 1412 in FIG. 14), and/or the drive train (e.g., drive train 1418 in FIG. 14). After the bailout handle 1550 has been rotated about 90 degrees, the user will rotate the bailout handle 1550 in the opposite direction (e.g., downward toward the motorized surgical handle assembly) and bailout bar will be moved distally.

Figure 15D:
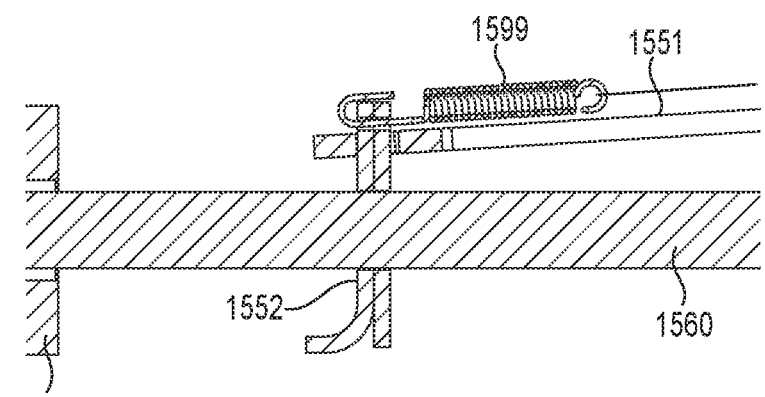

As shown in FIG. 15D, the force of bailout bar on toggle plates 1552 keep the toggle plates 1552 sufficiently orientated such that they do not bite into drive shaft 1560 but rather slide over it. At this point, the user can again rotate the bailout handle 1550 in an upward direction. In some embodiments described in this paragraph, the toggle plates 1552 are held in a perpendicular or relatively perpendicular relationship with the drive shaft 1560 so that the drive shaft 1560 freely moves through the toggle plates 1552. In these embodiments, the angle of the toggle plates 1552 relative to the drive shaft 1560, taking into account the diameter or the opening and thickness of the toggle plate(s) 1552, needs to be such that the drive shaft 1560 can move without interference from the toggle plates 1552. In some embodiments this is 85° to 95° or 88° to 92°.

Figure 16A:
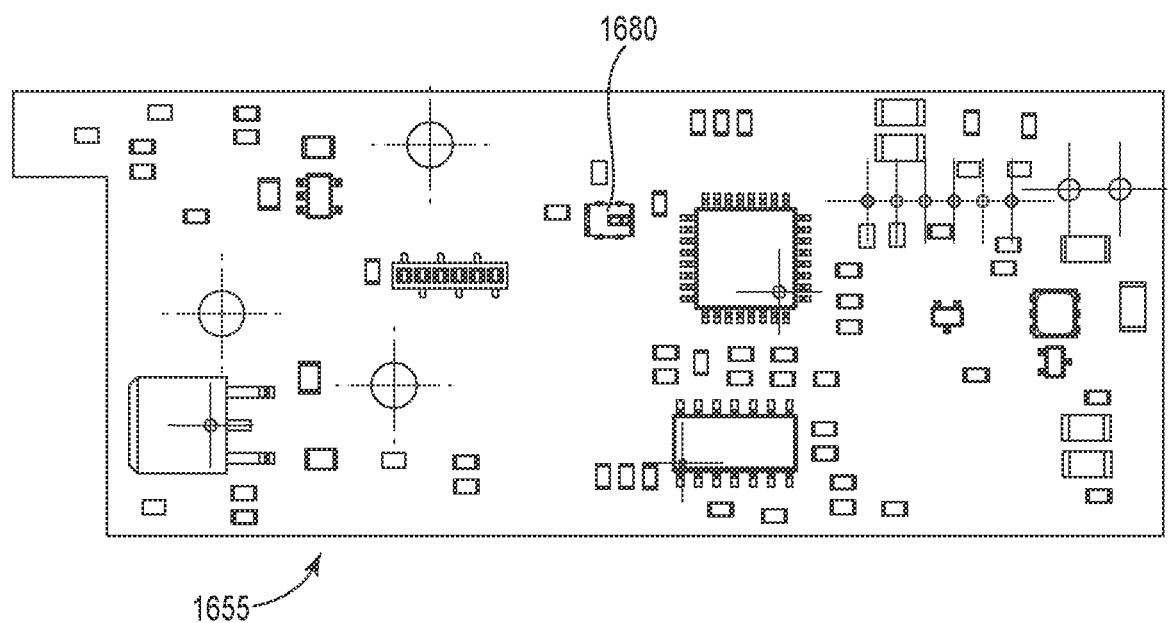
FIGS. 16A and 16B are schematic diagrams of a circuit board that could be used for a motorized surgical handle assembly in accordance with a number of embodiments of the present disclosure.
Figure 16B:
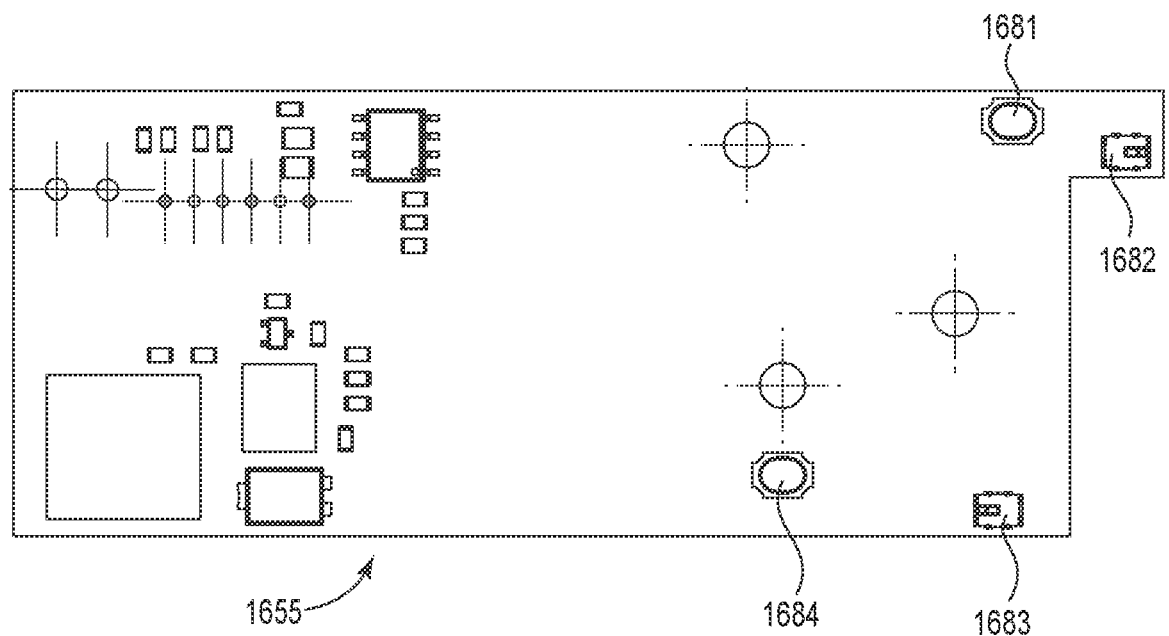

In some embodiments, a motorized surgical handle assembly (e.g., motorized surgical handle assembly 1302 in FIG. 3) is controlled by circuit board 1655 as shown in FIGS. 16A and 16B. FIG. 16A shows the top of circuit board 1655 and FIG. 16B shows the bottom. Circuit board 1655 may include a micro controller or microprocessor for controlling all the functions of the motorized surgical handle assembly, a motor driver, a voltage converter, and, as discussed herein, various switches.

For example, cam (e.g., cam 1357 in FIG. 13) hits (e.g., closes) reload switch 1682 to indicate that a reloadable cartridge assembly (e.g., reloadable cartridge assembly 103 in FIG. 1) is attached to the motorized surgical handle assembly. If no reloadable cartridge assembly is attached to the motorized surgical handle assembly, the motorized surgical handle assembly cannot be electrically activated.

Protrusion (e.g., protrusion 1497 in FIG. 14) on reverse cam 1465 hits reverse switch 1684 to cause the drive train (e.g., drive train 1418 in FIG. 14) to run in reverse. Protrusion (e.g., protrusion 1785 on selector cam (e.g., selector cam 1763 in FIG. 17) hits switch 1683 to put the motorized surgical handle assembly into a ready-to-fire mode.

When power trigger (e.g., power trigger 1310 in FIG. 13) is pulled, it presses protrusion (e.g., protrusion 1395 in FIG. 13) of an intermediate lever (e.g., intermediate lever 1354 in FIG. 13) into contact with power switch 1681 on circuit board 1655. In some embodiments, power switch 1681 is an open/close switch and the drive train receives relatively constant power. In some embodiments, power switch 1681 is a variable switch such as a variable resistor, varistor, potentiometer, or other analog sensor so that the harder power trigger is squeezed, the more power the drive train will receive and the faster it will run.

The u-shaped latch (e.g., u-shaped latch 1369 in FIG. 3) interacts with switch 1680 on circuit board 1655. When switch 1680 is closed by the contact of u-shaped latch, power is supplied to the circuit board 1655. When bailout handle (e.g., bailout handle 1550 in FIG. 15) is lifted and u-shaped latch is not in contact with switch 1680 (e.g., the switch is open), no power will flow to the circuit board 1655.

Motorized surgical handle assembly can be powered by a battery, which can be rechargeable or disposable, or by an AC power supply. If a rechargeable battery is used, the battery will be positioned so that it can be either removed or recharged. If a disposable battery is used, the handle will also include a drain so that the battery can be drained prior to disposal. If AC power is used, a power converter can be used to convert 120V or 240V AC, at either 50 or 60 Hz, to 24V, or any other suitable voltage, DC. In some embodiments, the handle will be supplied with a power cord that will plug in to the power converter.

This power can be supplied to the circuit board 1655. In some embodiments, the drive train is provided with 12V for the forward movement and 24V for the reverse. In some embodiments, the micro controller may control many features of the motorized surgical handle assembly. For example, no power will be supplied to the drive train if no reloadable cartridge assembly is attached to the motorized surgical handle assembly.

As is known in the art, many reloadable cartridge assemblies have a blade lock that is engaged after a reloadable cartridge assembly has been used so that the reloadable cartridge assembly cannot be accidentally used again. In some embodiments, the control system of the micro controller has a limit such as 0.2 to 0.3 amps for the first 5 to 10 mm of travel of the gear rack (e.g., gear rack 1421 in FIG. 14). In some embodiments, the control system of the micro controller has a limit such as 0.25 amps for the first 5 to 10 mm of travel. In the event that the blade lock would be engaged, the current to the motor would spike above this limit and the drive train would be stopped. In some embodiments, for the remaining stroke length, the limit can be 0.75 to 1.25 amps. In some embodiments, for the remaining stroke length, the limit can be 1.0 amps. This limit is set high enough for a surgical stapler, such as apparatus 100 in FIG. 1, to safely staple and cut through tissue, but when the surgical stapler reaches the end of the firing stroke, the limit will be hit, and the drive train will be stopped. At this time, the user can put the surgical handle assembly into reverse to retract the drive shaft.

Figure 17A:
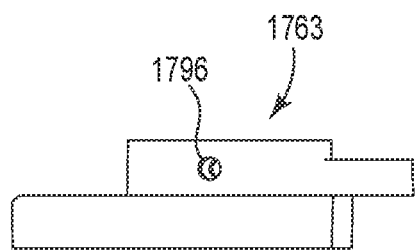
FIGS. 17A, 17B, and 17C are schematic diagrams of a selector cam that could be used for a motorized surgical handle assembly in accordance with a number of embodiments of the present disclosure.
Figure 17B:
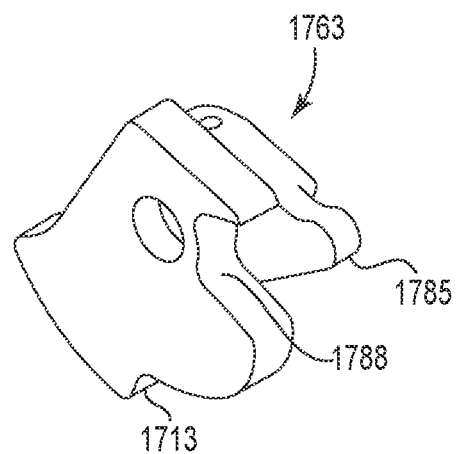
Figure 17C:
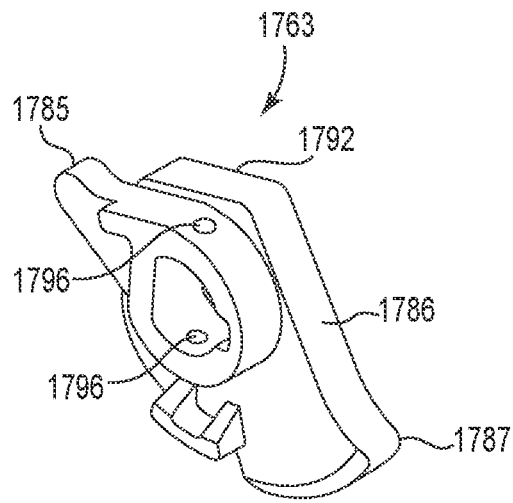

FIGS. 17A, 17B, and 17C show various views of selector cam 1763. FIG. 17A is a top view. FIG. 17B is a view from the side opposite the selector lever (e.g., selector lever 1417 in FIG. 14). FIG. 17C is from the side that faces the selector lever.

Shown is hole 1796 that houses pin (e.g., pin 1464 in FIG. 14) so that selector cam 1763 is non-rotationally fixed to the selector lever. Also shown is protrusion 1785. When selector lever is moved to the unlocked position, protrusion 1785 closes switch (e.g., switch 1683 in FIG. 6B) on circuit board (e.g., circuit board 1655 in FIGS. 6A and 6B) putting the motorized surgical handle assembly in the ready to fire position.

Shown in FIG. 17C are surfaces 1792, 1786, 1787 of selector cam 1763. As discussed with regard to FIG. 14, when assembled, spring (e.g., spring 1466 in FIG. 4) pushes reverse cam (e.g., reverse cam 1465 in FIG. 14) in a downward clockwise direction when situated as in FIG. 14.

When the selector lever is in the locked position, surface 1786 rests against the reverse cam and selector cam 1763 and selector lever are in a stable position.

When selector lever is rotated to the unlocked position, selector cam 1763 rotates such that surface 1792 is positioned against the reverse cam. The transition from surface 1786 to 1792 is not sufficient to cause reverse cam protrusion (e.g., protrusion 1497 in FIG. 14) to hit reverse switch (e.g., reverse switch 1684 in FIG. 6B) on the circuit board.

When the selector lever is rotated to the reverse position, selector cam 1763 rotates such that surface or tip 1787 is positioned against the reverse cam. This causes the reverse cam protrusion to hit the reverse switch (e.g., reverse switch 1684 in FIG. 6B) on the circuit board but it is not a stable position and the spring will force the selector lever back to the locked position after the physician/user releases the selector lever.

Also shown is concave locking opening 1713. When the movable handle is in a proximal position proximate to the non-movable handle and subsequently the selector lever and the selector cam 1763 are rotated to the unlocked position, locking protrusion (e.g., locking protrusion 1489 in FIG. 14) will be positioned in concave locking opening 1713 and will prevent the movable handle from opening (e.g., moving distally).

Figure 18A:
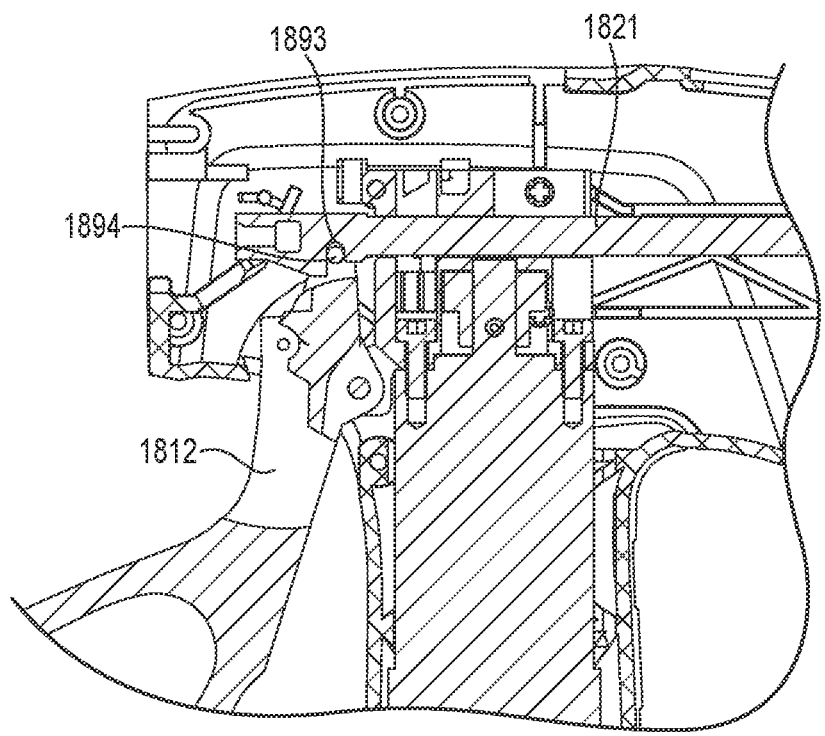
FIGS. 18A, 18B, and 18C show an example of a clamp and unclamp mechanism for a motorized surgical handle assembly in accordance with a number of embodiments of the present disclosure.
Figure 18B:
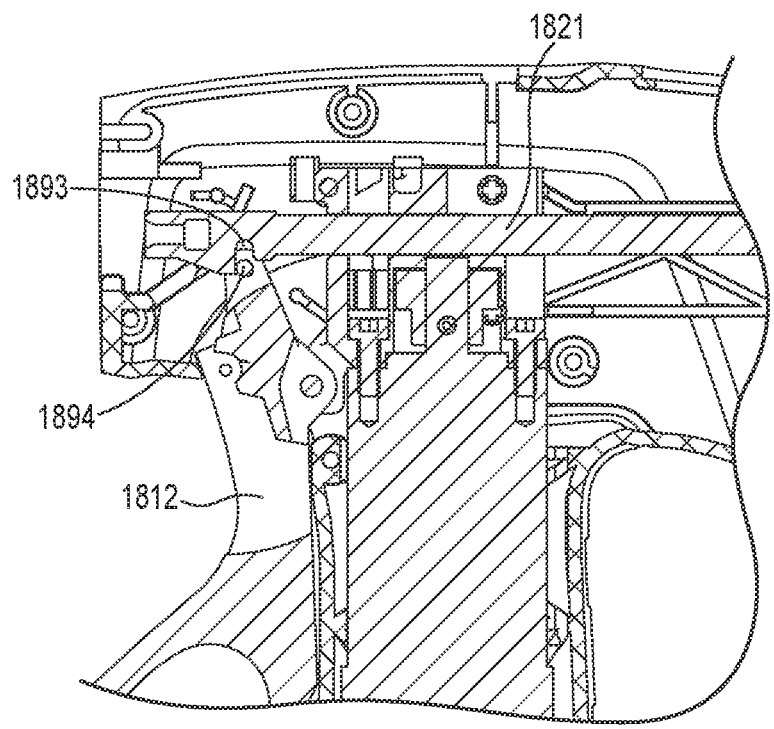
Figure 18C:
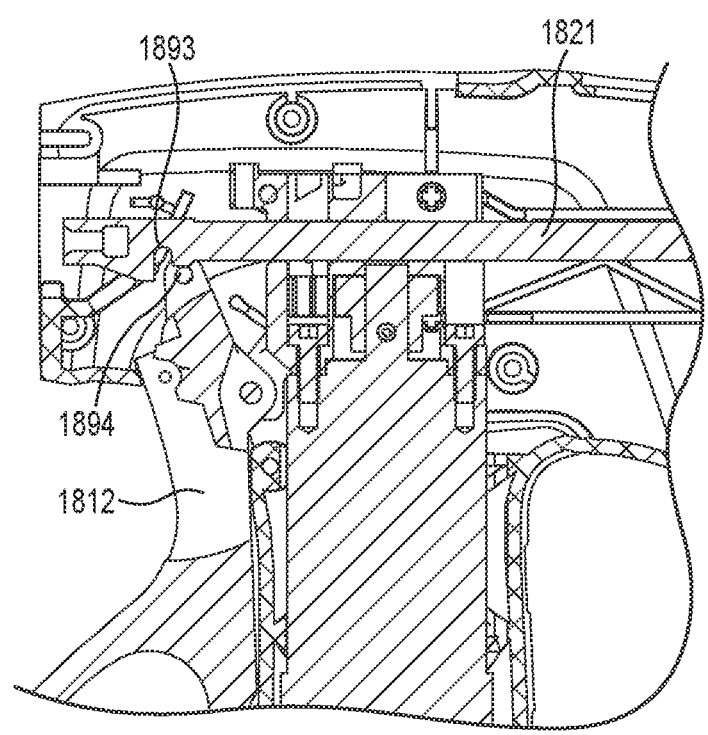

FIGS. 18A, 18B, and 18C show an example of the clamp and unclamp mechanism for a motorized surgical handle assembly (e.g., motorized surgical handle assembly 1302 in FIG. 13) in accordance with a number of embodiments of the present disclosure. FIG. 18A shows a portion of the motorized surgical handle assembly with gear rack 1821 in the clamping position. In the clamping position, rod 1894 is positioned within gear rack slot 1893, movable handle 1812 is in a distal position, and the jaws are in the open or unclamped position.

Gear rack slot 1893 has a general shape of an upside-down "U", with the distal leg of the "U" being longer than the proximal leg of the "U". When a user/physician squeezes movable handle 1812 and moves it to the proximal position, as rod 1894 is positioned above the movable handle 1812 pivot point, the rod 1894 will move in a distal direction. As rod 1894 is positioned in gear rack slot 1893, gear rack 1821 will be moved distally when movable handle 1812 is squeezed. This distal movement of gear rack 1821 will cause the jaws to close or clamp. In some embodiments, this distal movement causes an I-beam to move into contact with the two elongated members (e.g., elongated members 107 and 109 in FIG. 1) and causes them to move together.

In this position shown in FIG. 18B, rod 1894 is positioned beneath the shorter proximal leg of gear rack slot 1893 but still positioned against the longer, distal leg of gear rack slot 1893. At this stage, the user/physician can either move movable handle 1812 back to the distal position which will result in gear rack 1821 moving proximally and unclamping or opening the jaws, either manually or using the reverse setting of the selector lever or turn the selector lever to unlock and begin the firing (e.g., staple delivery) process.

FIG. 18C illustrates the position of gear rack 1821 after the user/physician has begun the firing process. As rod 1894 was positioned beneath the end of the shorter, proximal leg of gear rack slot 1893, it will not interfere with any distal movement of gear rack 1821. FIG. 18C shows that gear rack 1821 has moved distal of the clamping position shown in FIG. 18B and rod 1894 has moved out of gear rack slot 1893 and is positioned proximal to gear rack slot 1893.

As described above, when a user/physician uses the reverse position of the selector lever after delivering staples, the gear rack 1821 is returned to the position shown in FIG. 18B. At this point, the user/physician can either unclamp the jaws by manually moving movable handle 1812 distal or by turning selector lever to reverse and allowing the electric motor to open the jaws. FIG. 18A is the position that the control system will put the motorized surgical handle assembly in upon powering up of the motorized surgical handle assembly and attaching a reloadable cartridge assembly, provided that the reloadable cartridge assembly is not attached to the motorized surgical handle assembly at startup.

Figure 19A:
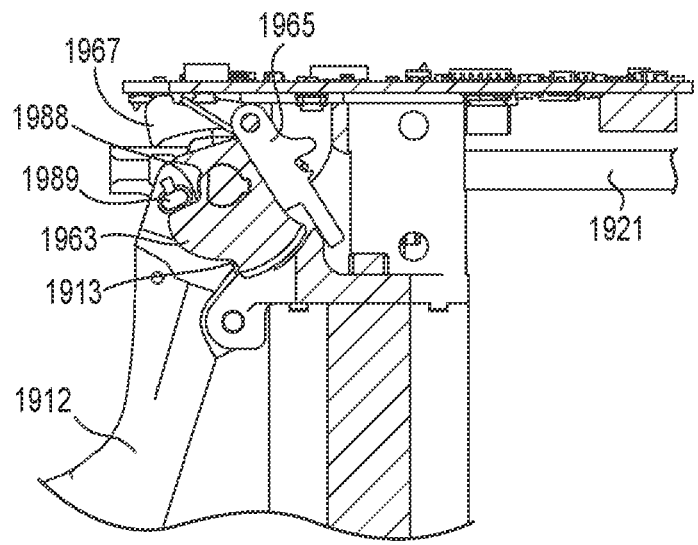
FIGS. 19A, 19B, 19C, and 19D show an example of a selector cam in various settings for a motorized surgical handle assembly in accordance with a number of embodiments of the present disclosure.

FIGS. 19A, 19B, 19C, and 19D show an example of a selector cam 1963 in various settings for a motorized surgical handle assembly (e.g., motorized surgical handle assembly 1302 in FIG. 13) in accordance with a number of embodiments of the present disclosure. FIG. 19A shows a portion of the motorized surgical handle assembly with the movable handle 1912 in a distal position and a selector lever (e.g., selector lever 1417 in FIG. 14) (not shown) in the locked position. In this position, locking protrusion 1989 is positioned against surface 1988 and prevents the selector cam 1963 (and the selector lever) from being rotated to the unlocked position or, in this figure, rotated clockwise.

Figure 19B:
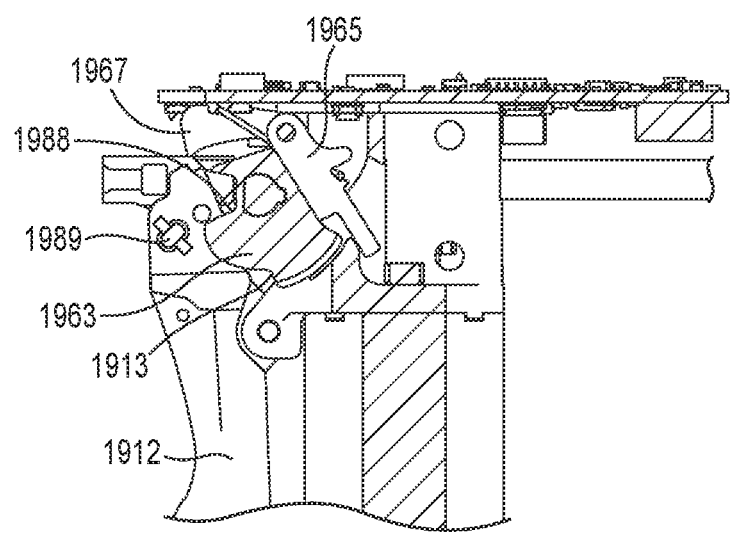

In FIG. 19B, movable handle 1912 has been moved to the proximal position and locking protrusion 1989 has moved out of contact with surface 1988 and/or selector cam 1963. Now, selector cam 1963 (and the selector lever) can be rotated to the unlocked position or, in this figure, rotated clockwise.

Figure 19C:
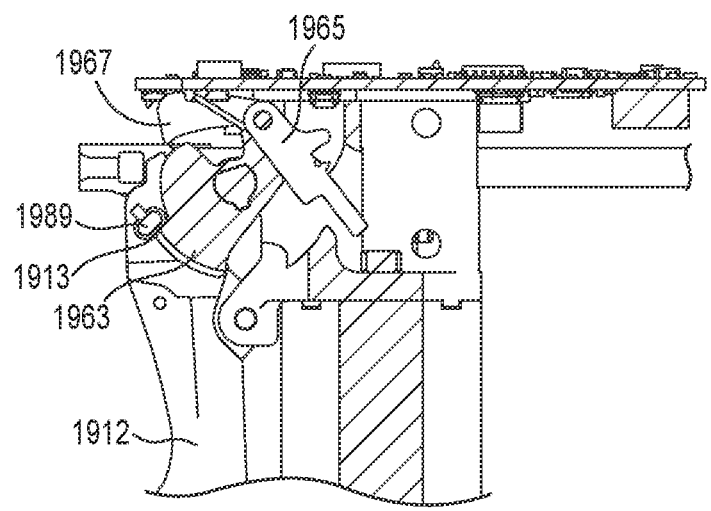

In FIG. 19C, the selector cam 1963 (and selector lever) has been rotated to the unlocked position to put the motorized surgical handle assembly in the ready to fire position. In this position, locking protrusion 1989 is now against concave locking opening 1913 of selector cam 1963. In this position, selector cam 1963 locks movable handle 1912 in the proximal position.

Figure 19D:
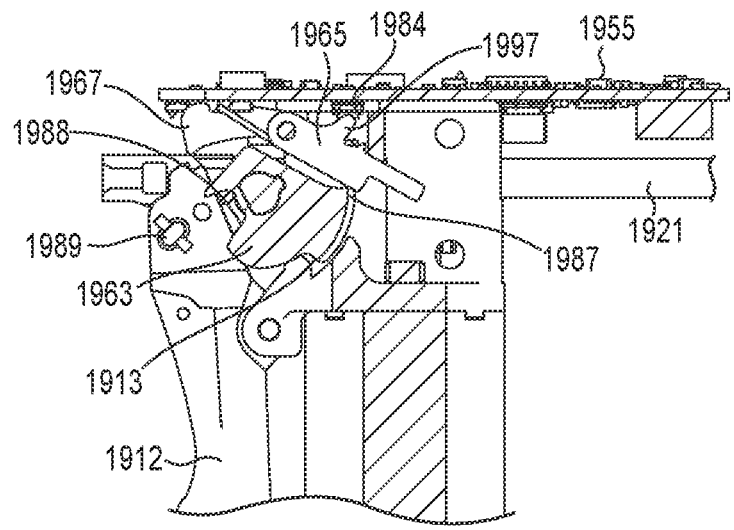

FIG. 19D shows the selector cam 1963 (and selector lever) in the reverse position. In this position, locking protrusion 1989 is no longer positioned against concave locking opening 1913 and the selector cam 1963 is no longer locking the movable handle 1912 in the proximal position. Here, if gear rack 1921 is in a position distal to the clamping position, locking cam 1967 will be positioned within notch (e.g., notch 1490 in FIG. 14) of movable handle 1912 and will be acting to lock the movable handle in the proximal position. If gear rack 1921 is in the clamping position, friction cam (e.g., friction cam 1353 in FIG. 13) will be positioned against movable handle 1912 and, through friction, holding the movable handle in the proximal position. Shown is reverse cam 1965 moved to an upward position by tip 1987 with protrusion 1997 in a position to close reverse switch 1984 of circuit board 1955.

As discussed herein, the circuit board 1955 of the motorized surgical handle assembly may include a microcontroller or microprocessor to control and/or automate various aspects of the motorized surgical handle assembly. For example, in some embodiments the microcontroller runs through a series of checks upon start up when the device is turned on or, in some embodiments, when it is plugged in. If no reloadable cartridge assembly (e.g., reloadable cartridge assembly 103 in FIG. 1) is attached, the microcontroller will reverse the drive train (e.g., drive train 1418 in FIG. 14) until the gear rack 1921 is in the proximal most position and the retraction spring (e.g., retraction spring 1356 in FIG. 3) is compressed. In some embodiments this is called the home position. At this point, upon detecting a current spike, the drive train will rotate the driving gear to move the gear rack 1921 distally a short distance by the unloading of the retraction spring. In some embodiments, this is called the loading position.

If, upon start up, a reloadable cartridge assembly is detected, no action will be taken. In some embodiments where the motorized surgical handle assembly is powered up with no reloadable cartridge assembly attached and where the control system moves the gear rack 1921 to the loading position, upon a reloadable cartridge assembly being attached, the control system will rotate the driving gear (e.g., driving gear 1043 in FIGS. 10A and 10B) a short distance, in some embodiments about 70°, while not moving driven gear (e.g., driven gear 1044 in FIGS. 10A and 10B) or gear rack 1921. This is the clamping or grasping position. This movement of the driving gear causes bosses (e.g., bosses 1045-1 and 1045-2 in FIG. 10B) to be positioned relative to bosses (e.g., bosses 1045-3 and 1045-4 in FIG. 10A) of the driven gear to allow space for the clamping motion, which moves the gear rack 1921 distally without interference from the bosses.

In some embodiments, an encoder is used with the drive train. The microcontroller can receive information from the encoder and will use the encoder information, for example, in setting the current limits for the distal movement of the gear rack 1921. In some examples, when the motorized surgical handle assembly is put into reverse, the reverse motion will continue until the gear rack 1921 is in a position wherein the movable handle 1912 can be used to open and close, unclamp and clamp, the jaws.

If the selector lever is again turned to the reverse setting, the gear rack 1921 will be moved to the proximal most position, whereupon it may be moved distally a small distance as described herein and the jaws will automatically unclamp. However, if while the gear rack 1921 is being reversed a physician/user moves the selector lever to the reverse or unlocked position or presses the power trigger (e.g., power trigger 1310 in FIG. 13), the reverse motion will stop. At this point the physician/user can again move the selector lever to reverse to continue the reverse action or move the selector lever to the unlocked position and move the gear rack 1921 distally.

In some embodiments, the microcontroller determines when the I-beam of the reloadable cartridge assembly is at its end of stroke by sensing a current spike in the drive train. When the current gets above a set point, the microcontroller will stop the drive train. In some embodiments, the microcontroller may rely on sudden current drops and/or sudden rises in current to indicate that there may be a problem somewhere in the surgical stapler. For example, a sudden drop in current may indicate a breakage somewhere in the surgical stapler and a sudden rise in current may indicate the end of a stroke, an obstruction, or tissue that is too thick or tough for the surgical stapler.

In some embodiments, artificial intelligence of the microcontroller may be used to capture the various signals from the surgical stapler and analyze the signals to determine if there are problems with the surgical stapler or if there are ways to improve the performance for the physician/user. In some embodiments, the encoder is used to inform the microprocessor of the relative position of the gear rack 1921. In this embodiment, the microprocessor could, for example, zero out the location indicator for the gear rack 1921 when the gear rack 1921 has compressed the retraction spring. In this example the microprocessor would then be able to determine when to switch from the low amp setting to the high amp setting and would be able to determine when the gear rack 1921 is properly positioned to allow for the movable handle 1912 to clamp and unclamp the jaws.

In some embodiments, it is important for the motor to immediately stop when the end of stroke is detected as continued movement of the drive train after the end of stroke is reached could result in damage to the reloadable cartridge assembly. In some embodiments, the software or control system of the microcontroller can use the motor speed and motor drive current to detect obstructions or potential obstructions in the path of the surgical stapler. In this embodiment, the control system can determine the difference between a hard tissue that the surgical stapler can progress through and an obstruction such as a piece of surgical equipment or the end of the reloadable cartridge assembly fire stroke and control the motor as appropriate.

In some embodiments, the control system can be preprogrammed with the various lengths of reloadable cartridge assemblies that may be used with the surgical handle. In this embodiment, the control system can be programmed to more quickly cut power if an obstacle is detected at any of these lengths in an effort to prevent damage to the reloadable cartridge assembly.

In some embodiments, a visible light, such as a LED, or audible system may be used to inform the user/physician of the status of the motorized surgical handle assembly. In this embodiment, for example, the light or LED could be green when everything is fine, flashing green when in the ready to fire position, yellow if a possible obstruction is detected, and red if the drive train is stopped for an obstruction including the end of firing stroke or if some other problem is detected. In some embodiments, the light can be an LED positioned beneath a transparent tradename on the top of the motorized surgical handle assembly. In some examples, the motorized surgical handle assembly could emit sound, such as, beeps which can change in pitch or frequency when there is a problem.

In a number of embodiments, a method of using a surgical stapler is provided. When positioning the surgical stapler for use, either in open surgery or through an instrument such as a trocar, the clinician may need to rotate and/or articulate the elongated members to position them properly. As the surgical stapler is used to clamp, staple, and cut tissue, in some instances the clinician needs to clamp and unclamp the elongated members to ensure that they are properly positioned. Once the elongated members are in position, the clinician can clamp the elongated members and deliver the staples. The cutter on the I-beam can cut the tissue as the staples are being delivered.

Some of the embodiments described herein have a motorized surgical handle assembly with a reloadable staple or cartridge assembly. The embodiments herein are equally applicable to a staple system where the reloadable cartridge is just a staple cartridge that is loaded into one of the elongated members.

In some embodiments discussed herein such as, for example, FIG. 3B, various components are shown as separate pieces. Multiple components can be formed as a single piece and still fall within the scope of the inventions discussed herein. In some embodiments discussed herein, the motorized surgical handle assembly may also have an on/off switch. In some embodiments discussed herein, the motorized surgical handle assembly will power up immediately upon being plugged in to a power source.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled. The terms proximal and distal, as used herein, are from the perspective of the clinician or other user of the device. The terms left and right, as used herein, are from the perspective of a clinician or other user holding apparatus (e.g., apparatus 100 in FIG. 1) in an upright position with non-movable handle (e.g., non-movable handle 1116 in FIG. 11) on the bottom.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A motorized surgical handle assembly apparatus, comprising:
    a non-movable handle;
    a movable handle configured to be moved away from and into proximity with the non-movable handle, wherein the movable handle comprises a locking protrusion;
    an electric motor operably coupled to the non-movable handle;
    a power trigger configured to selectively activate or deactivate the electric motor;
    a selector lever configured to rotate between (i) a locked position in which the power trigger is prevented from selectively activating or deactivating the electric motor and (ii) an unlocked position in which the power trigger is actuatable to selectively activate or deactivate the electric motor; and
    a selector cam coupled to the selector lever, wherein the selector cam comprises a surface with a concave locking opening, and wherein the selector cam is configured to rotate in response to the selector lever rotating;
    wherein, when the movable handle is in proximity with the non-movable handle and the selector lever is in the unlocked position, the surface with the concave locking opening is positioned adjacent to the locking protrusion to lock the movable handle in place.

2. The apparatus of claim 1, further comprising:
    a gear rack comprising a protrusion; and
    a locking cam;
    wherein, when the gear rack is positioned in a clamping position, the locking cam is positioned on the gear rack protrusion; and
    wherein, when the movable handle is in proximity to the non-movable handle and the gear rack is positioned in a position more distal than the clamping position, the locking cam is positioned in a notch on the movable handle to lock the movable handle in place.

3. The apparatus of claim 1, further comprising:
    a friction cam; and
    a spring coupled to the friction cam, wherein the spring is configured to bias the friction cam in a direction of the movable handle;
    wherein the friction cam is configured to interact with the movable handle to prevent un-forced movement of the movable handle.

4. The apparatus of claim 3, wherein the movable handle is in a proximal position when the friction cam is configured to interact with the movable handle to prevent un-forced movement of the movable handle.

5. The apparatus of claim 4, wherein the motorized surgical handle assembly is coupled to a reloadable cartridge assembly.

6. The apparatus of claim 5, wherein jaws of the reloadable cartridge assembly are clamped when the movable handle is in the proximal position.

7. The apparatus of claim 6, wherein the jaws are unclamped when the movable handle is moved distally.

8. The apparatus of claim 6, wherein the jaws are unclamped when the selector lever is rotated to a reverse position.

9. The apparatus of claim 1 wherein the selector lever (i) is configured to rotate from the locked position to the unlocked position in response to a first user-applied force and (ii) is configured to rotate from the unlocked position to the locked position in response to a second user-applied force.

10. The apparatus of claim 1 wherein the selector lever is configured to be rotatable from the locked position to the unlocked position only when the movable handle has moved into proximity with the non-movable handle.

11. The apparatus of claim 1 wherein the apparatus is tethered to a power cord and does not include a battery.

12. A motorized surgical assembly apparatus, comprising:
    a movable handle configured to pivot from a distal position to a proximal position where the movable handle is positioned adjacent to a non-movable handle, wherein when the movable handle is in the proximal position, jaws of a reloadable cartridge assembly are in a clamped position and wherein when the movable handle is in the distal position, the jaws are in an unclamped position;
    a gear rack, wherein the gear rack is in a proximal position when the movable handle is in the distal position and the gear rack is in a distal position when the movable handle is in the proximal position;
    a circuit board including a ready-to-fire switch;
    a selector lever; and
    a selector cam including a protrusion, wherein, when the selector lever is rotated to an unlocked position, the protrusion of the selector cam is moved into contact with the ready-to-fire switch and the motorized surgical handle assembly is switched to a ready-to fire mode,
    wherein, when the jaws are in the clamped position, the movable handle is configured to move the jaws to the unclamped position when the movable handle is moved from the proximal to the distal position, which moves the gear rack from the distal position to the proximal position; and
    wherein, when the jaws are in the clamped position, an electric motor is configured to move the gear rack from the distal position to the proximal position to move the jaws to the unclamped position when a reverse switch is contacted.

13. The apparatus of claim 12, further comprising a drive train configured to drive the gear rack in a proximal direction when the reverse switch is contacted.

14. The apparatus of claim 13, further comprising first and second handle halves that provide the non-movable handle when coupled together, wherein the first and second handle halves are configured to house the drive train.

15. The apparatus of claim 12, further comprising a power trigger, when pulled, the power trigger is configured to press a protrusion of an intermediate lever into contact with a power switch on the circuit board that provides power to a drive train.

16. The apparatus of claim 12 wherein the protrusion of the selector cam is configured to contact the ready-to-fire switch only while the selector lever is in the unlocked position.

17. A motorized surgical handle assembly apparatus, comprising:
 a driving gear;
 a driven gear;
 an electric motor; and
 a gear rack movable by the electric motor via the driving gear and the driven gear;
 wherein the driving gear and the driven gear each comprise a toothed circumference and first and second surfaces, wherein the first surface on the driving gear faces the first surface on the driven gear, and wherein the driving gear and the driven gear are configured to have noncontinuous contact such that the driven gear may rotate less than 360 degrees without causing rotation of the driving gear and thereafter further rotation of the driven gear will cause rotation of the driving gear.

18. The apparatus of claim 17, wherein the driving gear comprises at least one boss extending from its first surface and the driven gear comprises an opening on its first surface, wherein the boss is configured to fit inside the opening.

19. The apparatus of claim 17, wherein the driving gear comprises at least one boss extending from its first surface and the driven gear comprises at least one boss extending from its first surface wherein the two at least one bosses are configured to interact with each other.

20. The apparatus of claim 17, wherein the motorized surgical handle assembly is coupled to a reloadable cartridge assembly.

21. The apparatus of claim 20, wherein jaws of the reloadable cartridge assembly are configured to clamp and unclamp without causing rotation of the driving gear.

\* \* \* \* \*